United States Patent [19]

Lopez-Nieto et al.

[11] Patent Number: 6,110,667
[45] Date of Patent: Aug. 29, 2000

[54] PROCESSES, APPARATUS AND COMPOSITIONS FOR CHARACTERIZING NUCLEOTIDE SEQUENCES BASED ON K-TUPLE ANALYSIS

[75] Inventors: Carlos Eduardo Lopez-Nieto, Natick; Sanjay Kumar Nigam, Chestnut Hill, both of Mass.

[73] Assignee: Brigham and Women's Hospital, Boston, Mass.

[21] Appl. No.: 08/522,384

[22] PCT Filed: May 12, 1995

[86] PCT No.: PCT/US95/06032

§ 371 Date: Nov. 15, 1996

§ 102(e) Date: Nov. 15, 1996

[87] PCT Pub. No.: WO95/31574

PCT Pub. Date: Nov. 23, 1995

Related U.S. Application Data

[63] Continuation-in-part of application No. 08/242,887, May 16, 1994, abandoned.

[51] Int. Cl.[7] .............................. C12Q 1/68; C12P 19/34; C07H 21/04
[52] U.S. Cl. .......................... 435/6; 435/91.2; 536/24.33
[58] Field of Search .............................. 435/6, 91.2, 810; 536/24.33

[56] References Cited

U.S. PATENT DOCUMENTS

| | | | |
|---|---|---|---|
| 4,683,202 | 7/1987 | Mullis | 435/91 |
| 5,262,311 | 11/1993 | Pardee et al. | 435/91.2 |
| 5,437,975 | 8/1995 | McClelland et al. | 435/6 |

OTHER PUBLICATIONS

Lopez–Nieto et al., Nature Biotechnology 14(7), 857–861 (1996).
Science, vol. 244, May 5, 1989, Libert et al., "Selective amplification and cloning of four new members of the G protein–coupled receptor family", pp. 569–572, see entire document.
Griffais et al., Nucleic Acids Res. 19(14), 3887–3891 (1991).
Claverie et al., Meth. Enzymol. 183, 237–252 (1990).
Claverie et al., Nucleic Acids Res. 14(1), 179–196 (1986).
Nelson et al., Proc. Natl. Acad. Sci. USA 86, 6686–6690 (1989).

Primary Examiner—Kenneth R. Horlick
Attorney, Agent, or Firm—Morgan & Finnegan, L.L.P.

[57] ABSTRACT

A sample containing nucleotide sequences is characterized or "fingerprinted" by contacting it, or portions thereof, with of plurality of primer pairs; detecting nucleotide regions delineated by subsequences hydridized with each primer pair; determining a physical characteristic of each such detected region; and indexing such physical characteristics as a function of the primer pair that hydridized to the delineating subsequences of the corresponding region. An apparatus for fingerprinting a sample containing nucleotide sequences includes functionality for carrying out such a process. A kit of primers for use in characterizing, or fingerprinting, a sample comprising one or more nucleotide sequences is produced by a process identifying a first set of primers that hybridize with relative high frequency to respective antisense subsequences putatively present in the sample (or complementary subsequences thereof); identifying a second set of primers that hybridize with relative low frequency to respective sense subsequences putatively present in the sample (or complementary subsequences thereof); and, providing as the kit of primers at least selected primers common to both the first and second sets.

56 Claims, 11 Drawing Sheets

```
                       SEQUENCE LISTING

<160> NUMBER OF SEQ ID NOS: 122

<210> SEQ ID NO 1
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 1
aaccccatca                                                          10

<210> SEQ ID NO 2
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 2
atctactcca                                                          10

<210> SEQ ID NO 3
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 3
```

-continued atctgctggc                                                          10

<210> SEQ ID NO 4
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 4
caacagctgc                                                          10

<210> SEQ ID NO 5
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 5
caaccccatc                                                          10

<210> SEQ ID NO 6
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 6
caacctggcc                                                          10

<210> SEQ ID NO 7
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 7
caactacttc                                                          10

<210> SEQ ID NO 8
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 8
caccaactac                                                          10

<210> SEQ ID NO 9
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 9
catcatctac                                                          10

<210> SEQ ID NO 10
<211> LENGTH: 10
<212> TYPE: DNA
<213> ORGANISM: Unknown Organism

```
<220> FEATURE:
<223> OTHER INFORMATION: Description of Unknown Organism:  Primer

<400> SEQUENCE: 10
catcctcaac                                                              10

<210> SEQ ID NO 11
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 11
catcctcttc                                                              10

<210> SEQ ID NO 12
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 12
acatcctggt                                                              10

<210> SEQ ID NO 13
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 13
catcctggcc                                                              10

<210> SEQ ID NO 14
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 14
catcctggtg                                                              10

<210> SEQ ID NO 15
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 15
catctactcc                                                              10

<210> SEQ ID NO 16
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 16
catctccatc                                                              10
```

```
<210> SEQ ID NO 17
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 17
catctccttc                                                              10

<210> SEQ ID NO 18
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 18
catctgctgg                                                              10

<210> SEQ ID NO 19
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 19
ccaactactt                                                              10

<210> SEQ ID NO 20
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 20
ccatcatcta                                                              10

<210> SEQ ID NO 21
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 21
cccatcatct                                                              10

<210> SEQ ID NO 22
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 22
ccccatcatc                                                              10

<210> SEQ ID NO 23
<211> LENGTH: 10
<212> TYPE: DNA
<213> ORGANISM: Unknown Organism
<220> FEATURE:
<223> OTHER INFORMATION: Description of Unknown Organism: Primer
```

-continued

```
<400> SEQUENCE: 23
accaactact                                                          10

<210> SEQ ID NO 24
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 24
cctcatctac                                                          10

<210> SEQ ID NO 25
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 25
cctctgctgg                                                          10

<210> SEQ ID NO 26
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 26
cctgctggcc                                                          10

<210> SEQ ID NO 27
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 27
cctggaccgc                                                          10

<210> SEQ ID NO 28
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 28
cctggccatc                                                          10

<210> SEQ ID NO 29
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 29
ccttcatcct                                                          10

<210> SEQ ID NO 30
```

```
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 30
ccttctacct                                                                10

<210> SEQ ID NO 31
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 31
ccttcttcat                                                                10

<210> SEQ ID NO 32
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 32
ctacctggcc                                                                10

<210> SEQ ID NO 33
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 33
ctacttcctg                                                                10

<210> SEQ ID NO 34
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 34
accatgtaca                                                                10

<210> SEQ ID NO 35
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 35
ctctgctggc                                                                10

<210> SEQ ID NO 36
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 36
```
ctcttctggc                                                          10

<210> SEQ ID NO 37
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 37
ctgcccttct                                                          10

<210> SEQ ID NO 38
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 38
ctgctgctca                                                          10

<210> SEQ ID NO 39
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 39
ctgctggctg                                                          10

<210> SEQ ID NO 40
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 40
ctggaccgct                                                          10

<210> SEQ ID NO 41
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 41
ctggccatcg                                                          10

<210> SEQ ID NO 42
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 42
ctggccctgg                                                          10

<210> SEQ ID NO 43
<211> LENGTH: 10
<212> TYPE: DNA

```
<213> ORGANISM: Unknown Organism
<220> FEATURE:
<223> OTHER INFORMATION: Description of Unknown Organism: Primer

<400> SEQUENCE: 43
ctggccgtgg                                                              10

<210> SEQ ID NO 44
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 44
ctggccttca                                                              10

<210> SEQ ID NO 45
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 45
accccatcat                                                              10

<210> SEQ ID NO 46
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 46
ctggctgccc                                                              10

<210> SEQ ID NO 47
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 47
ctggctgggc                                                              10

<210> SEQ ID NO 48
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 48
ctggctgtgg                                                              10

<210> SEQ ID NO 49
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 49
ctgggctact                                                              10
```

```
<210> SEQ ID NO 50
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 50
cttcatcatc                                                                  10

<210> SEQ ID NO 51
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 51
cttcatcctc                                                                  10

<210> SEQ ID NO 52
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 52
cttcatcctg                                                                  10

<210> SEQ ID NO 53
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 53
cttcatcgtg                                                                  10

<210> SEQ ID NO 54
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 54
cttcctgctg                                                                  10

<210> SEQ ID NO 55
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 55
cttcctggtg                                                                  10

<210> SEQ ID NO 56
<211> LENGTH: 10
<212> TYPE: DNA
<213> ORGANISM: Unknown Organism
<220> FEATURE:
```

-continued

<223> OTHER INFORMATION: Description of Unknown Organism: Primer

<400> SEQUENCE: 56
accgctacct                                                                10

<210> SEQ ID NO 57
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 57
gacaggtaca                                                                10

<210> SEQ ID NO 58
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 58
gaccgctacc                                                                10

<210> SEQ ID NO 59
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 59
gaccgctact                                                                10

<210> SEQ ID NO 60
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 60
gcatcatcat                                                                10

<210> SEQ ID NO 61
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 61
gccattgctg                                                                10

<210> SEQ ID NO 62
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 62
gcccttcttc                                                                10

```
<210> SEQ ID NO 63
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 63
gcctggcctg                                                              10

<210> SEQ ID NO 64
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 64
gccttcatca                                                              10

<210> SEQ ID NO 65
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 65
gccttcatcc                                                              10

<210> SEQ ID NO 66
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 66
gctatgccaa                                                              10

<210> SEQ ID NO 67
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 67
acctggccat                                                              10

<210> SEQ ID NO 68
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 68
gctgcccttc                                                              10

<210> SEQ ID NO 69
<211> LENGTH: 10
<212> TYPE: DNA
<213> ORGANISM: Unknown Organism
<220> FEATURE:
<223> OTHER INFORMATION: Description of Unknown Organism:  Primer
```

```
<400> SEQUENCE: 69
gctgctgctc                                                          10

<210> SEQ ID NO 70
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 70
gctgctgctg                                                          10

<210> SEQ ID NO 71
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 71
gctggccttc                                                          10

<210> SEQ ID NO 72
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 72
gctggctgcc                                                         10

<210> SEQ ID NO 73
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 73
gctgggctac                                                          10

<210> SEQ ID NO 74
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 74
gctggtcatc                                                          10

<210> SEQ ID NO 75
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 75
ggccttcatc                                                          10

<210> SEQ ID NO 76
<211> LENGTH: 10
```

```
<212> TYPE: DNA
<213> ORGANISM: Unknown Organism
<220> FEATURE:
<223> OTHER INFORMATION: Description of Unknown Organism: Primer

<400> SEQUENCE: 76
ggctgcccta                                                              10

<210> SEQ ID NO 77
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 77
actacttcct                                                              10

<210> SEQ ID NO 78
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 78
ggctgccctt                                                              10

<210> SEQ ID NO 79
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 79
ggctgggcta                                                              10

<210> SEQ ID NO 80
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 80
gggctactgg                                                              10

<210> SEQ ID NO 81
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 81
ggtgctgccc                                                              10

<210> SEQ ID NO 82
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 82
```

-continued

```
gtcaccaact                                                          10

<210> SEQ ID NO 83
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 83
gtctacctgg                                                          10

<210> SEQ ID NO 84
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 84
gtgctggtgt                                                          10

<210> SEQ ID NO 85
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 85
gtggaccgct                                                          10

<210> SEQ ID NO 86
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 86
tcaacagcac                                                          10

<210> SEQ ID NO 87
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 87
tcaaccccat                                                          10

<210> SEQ ID NO 88
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 88
atcatctgct                                                          10

<210> SEQ ID NO 89
<211> LENGTH: 10
<212> TYPE: DNA
<213> ORGANISM: Unknown Organism
```

-continued

<220> FEATURE:
<223> OTHER INFORMATION: Description of Unknown Organism: Primer

<400> SEQUENCE: 89
tcaacctggc                                                              10

<210> SEQ ID NO 90
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 90
tcatcagctt                                                              10

<210> SEQ ID NO 91
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 91
tccttcatcc                                                              10

<210> SEQ ID NO 92
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 92
tctacctggc                                                              10

<210> SEQ ID NO 93
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 93
tctgctggct                                                              10

<210> SEQ ID NO 94
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 94
tctgggtggc                                                              10

<210> SEQ ID NO 95
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 95
tgaacctggc                                                              10

```
<210> SEQ ID NO 96
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 96
tgaccgctac                                                          10

<210> SEQ ID NO 97
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 97
tgcccttctt                                                          10

<210> SEQ ID NO 98
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 98
tgctcatcat                                                          10

<210> SEQ ID NO 99
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 99
tgctgctcat                                                          10

<210> SEQ ID NO 100
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 100
tgctgctgct                                                          10

<210> SEQ ID NO 101
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 101
tgctggctgc                                                          10

<210> SEQ ID NO 102
<211> LENGTH: 10
<212> TYPE: DNA
<213> ORGANISM: Unknown Organism
<220> FEATURE:
<223> OTHER INFORMATION: Description of Unknown Organism: Primer
```

```
<400> SEQUENCE: 102
tgctggtcat                                                              10

<210> SEQ ID NO 103
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 103
tgctggttcc                                                              10

<210> SEQ ID NO 104
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 104
tggaccgcta                                                              10

<210> SEQ ID NO 105
<211> LENGTH: 9
<212> TYPE: DNA
<213> ORGANISM: Unknown Organism
<220> FEATURE:
<223> OTHER INFORMATION: Description of Unknown Organism: Primer

<400> SEQUENCE: 105 tggccatcg                                                               9

<210> SEQ ID NO 106
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 106
tggccatcgt                                                              10

<210> SEQ ID NO 107
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 107
tggctgccct                                                              10

<210> SEQ ID NO 108
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 108
tggctgggct                                                              10

<210> SEQ ID NO 109
```

```
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 109
tgggctactg                                                              10

<210> SEQ ID NO 110
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 110
tggtggctgt                                                              10

<210> SEQ ID NO 111
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 111
ttcatcatca                                                              10

<210> SEQ ID NO 112
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 112
ttcatcatct                                                              10

<210> SEQ ID NO 113
<211> LENGTH: 11
<212> TYPE: DNA
<213> ORGANISM: Unknown Organism
<220> FEATURE:
<223> OTHER INFORMATION: Description of Unknown Organism:  Primer

<400> SEQUENCE: 113
tcctgcgtgg c                                                            11

<210> SEQ ID NO 114
<211> LENGTH: 11
<212> TYPE: DNA
<213> ORGANISM: Unknown Organism
<220> FEATURE:
<223> OTHER INFORMATION: Description of Unknown Organism:  Primer

<400> SEQUENCE: 114
tgctgcgtca t                                                            11

<210> SEQ ID NO 115
<211> LENGTH: 10
<212> TYPE: DNA
<213> ORGANISM: Unknown Organism
<220> FEATURE:
<223> OTHER INFORMATION: Description of Unknown Organism:  Primer

<400> SEQUENCE: 115
```
tcatcatggg                                                          10

<210> SEQ ID NO 116
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 116
tcatcctcac                                                          10

<210> SEQ ID NO 117
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 117
tcatctacac                                                          10

<210> SEQ ID NO 118
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 118
tcatctactg                                                          10

<210> SEQ ID NO 119
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 119
tcatctcctt                                                          10

<210> SEQ ID NO 120
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 120
tcatctgctg                                                          10

<210> SEQ ID NO 121
<211> LENGTH: 10
<212> TYPE: DNA
<213> ORGANISM: Unknown Organism
<220> FEATURE:
<223> OTHER INFORMATION: Description of Unknown Organism: Primer

<400> SEQUENCE: 121
tcctgctggc                                                          10

<210> SEQ ID NO 122
<211> LENGTH: 10
<212> TYPE: DNA

```
<213> ORGANISM: Unknown Organism
<220> FEATURE:
<223> OTHER INFORMATION: Description of Unknown Organism:  Primer

<400> SEQUENCE: 122
tcctggtggc                                                           10
```

PROCESSES, APPARATUS AND COMPOSITIONS FOR CHARACTERIZING NUCLEOTIDE SEQUENCES BASED ON K-TUPLE ANALYSIS

This application is a Rule 371 national phase filing of PCT application No. PCT/US 95/06032, which is a continuation-in-part of application Ser. No. 08/242,887, filed on May 16, 1994, abandoned. Each of the patent applications referred to above is incorporated by reference herein in its entirety.

BACKGROUND OF THE INVENTION

The invention relates to characterizing, or "fingerprinting," nucleic acid sequences. It has application in the identification, cloning and analysis of genes, as well as in the diagnosis of disease.

Human genes were initially identified by isolation of their translate products (proteins), amino acid microsequencing, back translation to nucleotide sequences and hybridization of oligonucleotide probes designed from those nucleotide sequences. Protein isolation and purification were a major limitation of this approach.

Positional cloning, or reverse genetics, emerged as a more powerful technique. Taking advantage of physical proximity of genes and polymorphic sequences in the genome, linkage analysis led to the discovery of genes whose protein products were unknown. The positional markers initially used were restriction fragment length polymorphisms (RFLPs); subsequently, sequence target sites (STSs) were preferred. Due to the roaring success of positional cloning as a searching tool for disease genes, the scientific community has embarked on the ambitious project of creating a physical map (based on STSs) of the entire human genome.

As the number of genes identified and sequenced has increased, scientists have developed a new strategy of gene isolation. By aligning amino acid sequences of related genes and analyzing their homology, new proteins that are related to previously identified sequences in the same or other species have been identified either by screening libraries or by polymerase chain reaction (PCR). Although a technically simple and efficient approach, its usefulness is generally limited to proteins that are homologous to previously identified sequences.

A recent non-specific cloning method disclosed by Pardee, et al, U.S. Pat. No. 5,262,311, isolates messenger ribonucleic acids (mRNAs), reverse transcribes them to produce complementary deoxyribonucleic acids (cDNAs), and amplifies their 3' untranslated region by polymerase chain reaction (PCR) with sets of oligonucleotide primers. A first primer in each set hybridizes with the polyA tail and the two nucleotides immediately upstream to it. The second primer, which hybridizes to a sequence still further upstream, is said to comprise a arbitrary sequence of at least 9 and, preferably, of at least 13 nucleotides. It is understood by the inventors hereof that, in accord with actual practice, Pardee et al's second primer hybridizes with the specificity of a 6 to 7-mer.

Although the Pardee et al technique, commonly known as differential display PCR (DD-PCR), constitutes a significant advance, it is not without theoretical and practical limitations. To begin, assuming that the second primers "act" as 6 or 7-mers, a set of 20 will hybridize with a combined average frequency of one in 500. Presuming a normal distribution, roughly half of the sequences targeted by these primers will be more than 500 nucleotides from the polyA tail and, hence, will not be effectively resolved in a conventional electrophoresis gel. Because some mRNAs lack a polyA tail and others are shorter than 500 nucleotides, there is reduced likelihood of obtaining a PCR product. Still further, sequences immediately adjacent the polyA tail will most likely code for untranslated regions that are not necessarily well conserved and that are usually underrepresented in genomic databases. In order to obtain protein-coding sequence, a significant amount of sequencing and DNA library screening are usually required. These steps are laborious and time-consuming. Furthermore, because DD-PCR targets the polyA tail, it can only be applied to mRNA samples.

In view of the foregoing, an object of the invention is to provide improved processes, apparatus and compositions for characterizing, or "fingerprinting," nucleotide sequences. A further objects is to provide such processes, apparatus and compositions for use inter alia in mapping of genomic DNA, the selective identification and isolation of nucleotide sequences, the understanding of functional relationships between such sequences, and the diagnosis of disease. These and other objects are evident in the discussion that follows.

SUMMARY OF THE INVENTION

The aforementioned and other objects are attained by the invention, which provides in one aspect a process for characterizing a sample of nucleic acid by contacting it, or portions thereof, with of plurality of primer pairs; detecting nucleotide regions delineated by subsequences hybridized with each primer pair; determining a physical characteristic of each such detected region; and indexing such physical characteristics as a function of the primer pair that hybridized to the delineating subsequences of the corresponding region.

According to this aspect, each primer pair includes a so-called 5' primer and a so-called 3' primer (named for the relative end of the sense strand that they or their complements target). Each 5' primer is selected to hybridize with relative high frequency to a specific respective nucleotide subsequence putatively present in the sample (or a complementary subsequence thereof). Likewise, each 3' primer is selected to hybridize to a different respective nucleotide subsequence putatively present in the sample (or a complementary subsequence thereof). Those skilled in the art will appreciate that word "complementary" as used herein is synonomous with the term "reverse complementary" as that term is normally applied in reference to the complementary strand sequences.

In a related aspect of the invention, nucleotide regions targeted by the delineating primer pairs are detected by amplifying those regions, or their complementary sequences, e.g., through polymerase chain reaction (PCR). In this regard, the 3' primers are selected to hybridize with sense strand nucleotide subsequences that lie "downstream" of the antisense strand-hybridizing 5' primers of their respective pairs, and that are complementary to the 5' primers of the other pairs. Thus, the 5' primers can include oligonucleotide sequences that hybridize with high frequency to antisense strands amplified by PCR, but that hybridize with relative low frequency to sense strands amplified by that reaction. As discussed below, in one prefered practice of the invention, each primer pair can be applied "independently," i.e., to a separate respective portion of the sample.

The invention provides, in further aspects, a process as described above for use with a sample containing mRNA sequences (as opposed to genomic DNA, which can also be used as initial sample). In this regard, the process includes pre-treating the sample to produce cDNA. This can be carried out by contacting respective portions of the sample with the 3' primer that will be used in the subsequent PCR amplification and elongating those 3' primers (e.g., with reverse transcriptase) to form the complementary DNA.

A process of the invention can, in other aspects, determine for each nucleotide region targeted by the delineating primer pairs a physical characteristic including a molecular weight or length. This can be accomplished, for example, by gel electrophoresis.

Having once determined the physical characteristic, e.g. weight or length, of each nucleotide region targeted by a delineating primer pair, a process according to the invention can index that characteristic as a function of the identity of the primer pair itself. A compilation of such indexed characteristics, e.g., in database, graphical or matrix form, serves as a set of fingerprints of the different nucleotide sequences that compose the sample.

In another aspect, the invention contemplates comparing a compilation of indexed characteristics of a candidate sample (e.g., from a cancerous cell line) with the characteristics of a reference sample (e.g., a sample from a normal cell line) to determine the relative nucleotide content of those samples. The indexed characteristics of a candidate sample can also be analyzed independently, e.g., to determine the relative position of nucleotide sequences contained therein.

Still other aspects of the invention provide an apparatus with functionality for carrying out the processes described above.

The invention also provides a kit of primers for use in characterizing, or fingerprinting, a nucleic acid sample comprising one or more nucleotide sequences. According to one of the invention, that kit is produced by a process identifying a first set of primers that hybridize with relative high frequency to respective antisense subsequences putatively present in the sample (or complementary subsequences thereof); identifying a second set of primers that hybridize with relative low frequency to respective sense subsequences putatively present in the sample (or complementary subsequences thereof); and, providing as the kit of primers at least selected primers common to both the first and second sets.

The kit can be produced by a process as above including the further step of identifying a third set of primers, pairs of which hybridize to nucleotide subsequences in the sample (or complementary subsequences thereof) that delineate nucleotide sequence regions having quantifiable physical characteristics falling within a selected range. Those physical characteristic can include, for example, a molecular weight or length within a range resolvable by a detection apparatus, such as the 50 to 600 base pair length resolvable by gel electrophoresis apparatus. A kit of primers, according to this aspect, can be produced by selecting primers common to the first, second and third sets.

In still another aspect, the invention provides a kit produced by the above process including the step of identifying a set of primers of that anneal under substantially similar conditions of polymerase chain reaction. This can include identifying a subset of primers that hybridize with specific nucleotide sequences in the sample (or complementary sequences thereof) of substantially similar length, as well as a subset of primers have substantially similar GC content. The lengths can be, for example, between 5 and 20 nucleotides, 6 and 12 nucleotides, 7 and 9 nucleotides or, preferably, 8 nucleotides. The GC content can be, for example, between 50% and 75% or between 25% and 50%. A kit produced utilizing these steps can include primers common to all of selected ones of these sets and subsets.

Constituents of a kit produced as above can be winnowed by comparing the putative selectivities of respective groupings of primers within the larger set. Thus, for example, where the kit is to include (m) of the (n) primers common to selected sets described above, up to (m) candidate primers can be selected based on their individual selectivities vis-à-vis an actual or simulated biological sample. Further primers can be substituted for (m) primers so chosen to determine whether those further primers achieve still greater selectivity in conjunction with others of those (m) primers.

In still other aspects, the invention provides a kit of primers for targeting human protein coding regions including 5' primers selected from a group of 151 oligonucleotides including

| | | | | | | |
|---|---|---|---|---|---|---|
| aacctgga | aagaggag | aagcagga | aagctgga | aaggagac | aaggagct | aaggagga |
| aaggaggc | aaggccaa | acaagctg | accagaag | accccaag | accctgga | acctgaag |
| acctgctc | acctggaa | acctggac | acctggag | agaacctg | agaagagc | agaaggac |
| agaaggcc | agaccctg | agacctgg | agaggaga | agaggagc | agatcctg | agatgcag |
| agcctgga | aggacaag | aggagaac | aggccaag | agtggaag | atcctgga | atgaggag |
| atgctgga | caacccca | caacctgg | caagaagc | caagaagg | caagcaga | caagcagc |
| caagctgc | caagctgg | caaggaag | caaggaca | caaggaga | caaggagc | caaggagg |
| caaggtgg | caccaaga | caccaagg | cagaagac | cagaagct | catcaagg | catcgtgg |
| catgaagg | ccaagaag | ccaagcag | ccaagctg | ccaaggag | ccagagga | ccagatga |
| ccatcaag | ccctgaag | ccctgatg | cctcacca | cctgaagg | cctgagga | cctggaaa |
| cctggaga | cctggtgt | ctacctgg | ctgacctg | ctgcagaa | ctgccaag | ctggacaa |
| ctggacct | ctggagac | ctggccaa | ctggcgaa | ctgtggaa | ctgtggac | ctgtggag |
| gaacctgg | gaagccaa | gaagctga | gaaggaag | gaaggaca | gaagtgga | gacaagga |
| gacccaga | gaccctga | gacctgct | gacctgga | gagaagag | gagaagct | gagaagga |
| gagctgaa | gaggacct | gaggagat | gaggccaa | gatcctgg | gatgcaga | gatgtgga |
| gcaagaag | gccaagaa | gccaagga | gctgaagc | ggaagaga | ggacaaga | ggagaaag |
| ggagaaca | ggagaacc | ggagaatg | ggagatgc | ggagcaga | ggaggagt | ggccaaga |
| gtggacat | gtggagaa | gtggagac | gtggagct | tacctgga | tcaagcag | tcaaggag |
| tcaccaag | tcaccctg | tccctgga | tcctggac | tctgtgga | tgaccctg | tgaggagg |
| tgctgagc | tgctggac | tggaagtg | tggacaag | tggaccag | tggacctg | tggagaac |
| tggagacc | tggagaga | tggagagc | tggaggac | tggaggct | tggatgag | tggccaag |
| tggtggac | tgtgcctg | tgtggaca | tgtggaga | | | |

The size of that group can range from 1 to 5, 5 to 10, 10 to 20, 30 to 50 or 50 or more of these oligonucleotides. Still preferably, the 5' primers for targeting human protein coding regions are selected from the group of 30 oligonucleotides comprising

| | | | | | | |
|---|---|---|---|---|---|---|
| aagcagga | agaaggcc | agaccctg | agaggagc | atgctgga | caaggaga | catcgtgg |
| catgaagg | ccaagaag | ccagatga | cctcacca | cctgaagg | cctgagga | cctggaaa |
| cctggaga | ctacctgg | ctgcagaa | ctgccaag | gaagctga | gaagtgga | gacctgga |
| gagctgaa | gaggagat | ggagaaag | gtggagaa | tcctggac | tgctgagc | tggacaag |
| tggacctg | tggagaga | | | | | |

3' primers for inclusion in such kits can be selected as complements of the selected 5' primers.

In still other aspects, the invention provides a kit of primers for targeting G-protein coupled receptors including 5' primers selected from a group of 121 decanucleotides including:

| | | | | |
|---|---|---|---|---|
| aaccccatca | acatcctggt | accaactact | accatgtaca | accccatcat |
| accgctacct | acctggccat | actacttcct | atcatctgct | atctactcca |
| atctgctggc | caacagctgc | caaccccatc | caacctggcc | caactacttc |
| caccaactac | catcatctac | catcctcaac | catcctcttc | catcctggcc |
| catcctggtg | catctactcc | catctccatc | catctccttc | catctgctgg |
| ccaactactt | ccatcatcta | cccatcatct | ccccatcatc | cctcatctac |
| cctctgctgg | cctgctggcc | cctggaccgc | cctgccatc | ccttcatcct |
| ccttctacct | ccttcttcat | ctacctggcc | ctacttcctg | ctctgctggc |
| ctcttctggc | ctgcccttct | ctgctgctca | ctgctggctg | ctggaccgct |
| ctggccatcg | ctggccctgg | ctggccgtgg | ctggccttca | ctggctgccc |
| ctggctgggc | ctggctgtgg | ctgggctact | cttcatcatc | cttcatcctc |
| cttcatcctg | cttcatcgtg | cttcctgctg | cttcctggtg | gacaggtaca |
| gaccgctacc | gaccgctact | gcatcatcat | gccattgctg | gcccttcttc |
| gcctggcctg | gccttcatca | gccttcatcc | gctatgccaa | gctgccttc |
| gctgctgctc | gctgctgctg | gctggccttc | gctggctgcc | gctgggctac |
| gctggtcatc | ggaccgctac | ggccttcatc | ggctgcccta | ggctgcccttt |
| ggctgggcta | gggctactgg | ggtgctgccc | gtcaccaact | gtctacctgg |
| gtgctggtgt | gtggaccgct | tcaacagcac | tcaaccccat | tcaacctggc |
| tcatcagctt | tcatcatggg | tcatcctcac | tcatctacac | tcatctactg |
| tcatctcctt | tcatctgctg | tcctgctggc | tcctggtggc | tccttcatcc |
| tctacctggc | tctgctggct | tctgggtggc | tgaacctggc | tgaccgctac |
| tgcccttctt | tgctcatcat | tgctgctcat | tgctgctgct | tgctggctgc |
| tgctggtcat | tgctggttcc | tggaccgcta | tggccatcgc | tggccatcgt |
| tggctgccct | tggctgggct | tgggctactg | tggtggctgt | ttcatcatca |
| ttcatcatct | | | | |

The size of that group can range from 1 to 5, 5 to 10, 10 to 20, 30 to 50 or 50 or more of these decanucleotides. Still preferably, the 5' primers for targeting targeting G-protein coupled receptors are selected from the group of 20 decanucleotides comprising:

| | | | | |
|---|---|---|---|---|
| caaccccatc | catcctggtg | catctccatc | cctggccatc | ccttcatcct |
| cttcctgctg | gacaggtaca | gcctggcctg | gctatgccaa | gctgctgctg |
| gctggctgcc | gctgggctac | ggaccgctac | ggccttcatc | tcctg(c,g)tggc |
| tctgctggct | tctgggtggc | tgctcatcat | tgctg(c,g)tcat | tggtggctgt |

Related aspects of the invention concern use of such primers in the processes and apparatus described above.

These and other aspects of the invention are evident in the attached drawings and in the description that follows.

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Overview

Whereas the prior art techniques for gene analysis were originally conceived for the identification of genes in an individual, or stepwise, fashion, we describe below new processes, apparatus and compositions for both individual and large-scale gene identification. Based on detailed analysis of a large population of randomly selected human protein coding regions, we have found that there is sufficient low-level homology in the sense strands of such regions to permit highly selective screening, isolation and identification of at least the transcriptionally active human genome.

In the sense strand of coding regions, nucleotides combine in triplets (codons) to specify all different amino acids in proteins. The distribution of frequencies of 6 to 9-tuples in human coding regions is determined by the distribution of amino acids and combination of amino acids in human proteins, and by codon usage preference. K-tuples that represent the preferred codons of common amino acids that frequently combined with each other are likely to have a higher frequency. For example, we found that the 6-tuple "ctggag" which in frame codes for the amino acids leucine and glutamic acid occurs 2,087 times in the sense strand (all three possible frames) of 1,000 human coding regions (1,631,763 nucleotides), for an actual frequency of 1 in 781.9, which is more than 5 times the expected frequency assuming a random distribution (1 in 4,096).

Primers pairs that hybridize to certain statistically selected k-tuples are applied to a sample, so that nucleotide regions delineated by each pair of k-tuples can be identified. In a preferred practice, those regions are detected by exponential amplification using polymerase chain reaction (PCR).

Separation of the amplified products using electrophoretic gels allow their classification by size, as indexed by the identity of the delineating primer pair. That classification can be beneficially presented in terms of identities of the 3' and 5' primers so as to produce a three-dimensional matrix or fingerprint, i.e., 5' primer identity×3' primer identity× amplified product size, for each sample. Using the statistically designed primer set described herein, and based on a simulation using 1,100 human mRNAs, it appears that more than 70% of known (and potentially unknown) human genes are representable in such a matrix.

Characterization of Sample

Figure 1:
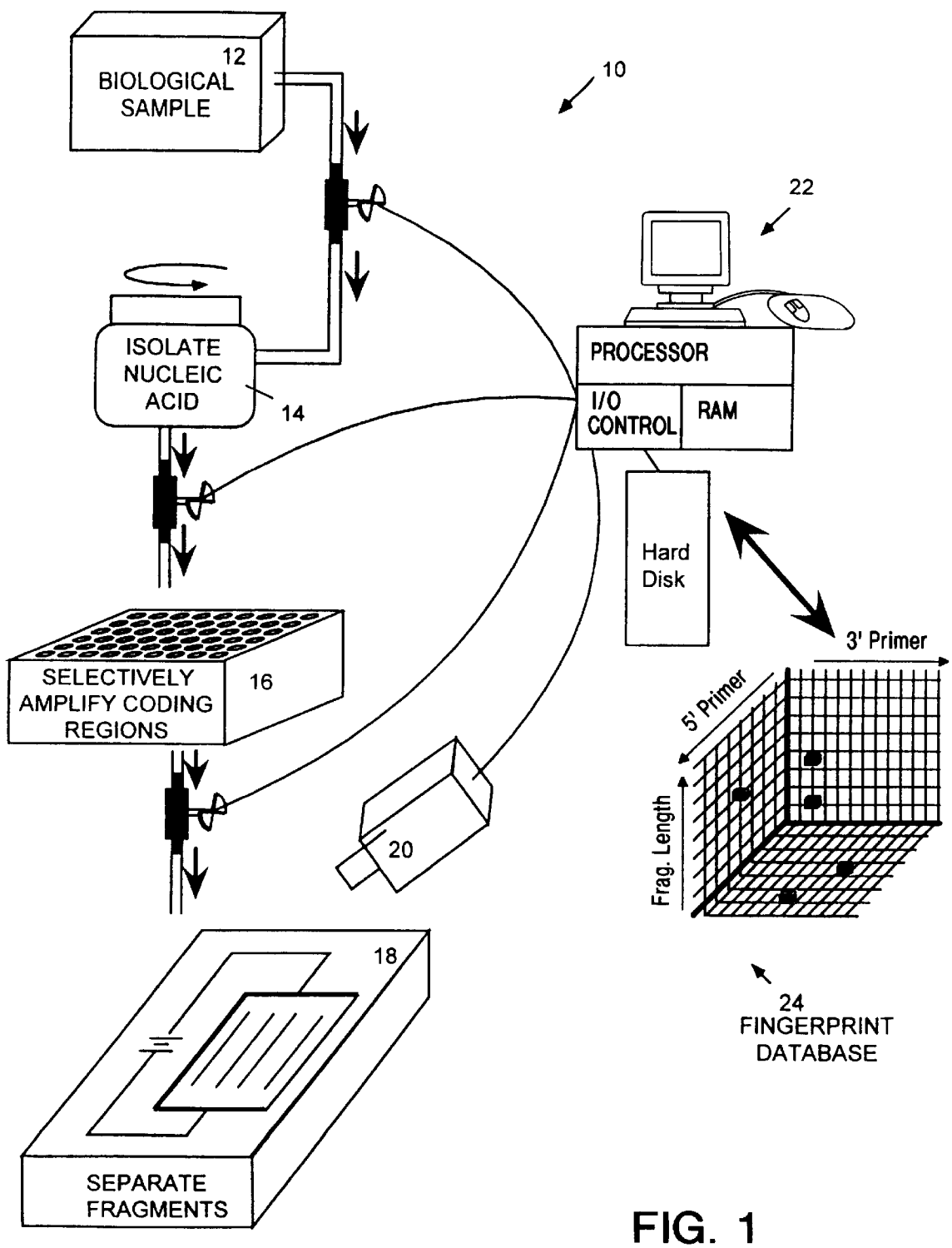
FIG. 1 depicts an apparatus 10 according to the invention for characterizing nucleotide sequences in a biological sample.

FIG. 1 depicts an apparatus 10 according to the invention for characterizing nucleotide sequences in a biological sample. The apparatus 10 includes a source 12 of biological sample; apparatus 14 for isolating nucleic acid, e.g., mRNA from the sample; apparatus 16 for selectively amplifying nucleotide sequences or fragments from that nucleic acid; apparatus 18 for separating those amplified fragments; video camera 20 for generating a digital image of the separated fragments; and control and analysis unit 22 for interpreting that image to generate a "fingerprint" of the sample.

In the preferred embodiments described below, elements 12–22 constitute stand-alone apparatus controlled by a human operator, who moves materials between them. In another preferred embodiment, such operation is automated by use of conventional robotics mechanisms or flow-control apparatus, with control signals emanating from control and analysis unit 22, as shown.

Source 12 represents a source of biological materials to be characterized in accord with the teachings herein. Those samples, which can derive from viral, bacterial, animal, plant or other such sources, contain nucleic acids to be characterized. While the embodiments described below are directed to the characterization of human mRNA, those skilled in the art will appreciate that teachings herein can be applied to the characterization of other nucleic acids (e.g. fragments of human genomic DNA contained in vectors, cosmids or YACs). Furthermore, nucleic acids from related and other species may be characterized as well (e.g. mouse—see Example 2, below).

Element 14 represents conventional apparatus and methods for isolating nucleic acids from the sample. In a preferred embodiment, element 14 comprises a centrifugal separation apparatus for operation in a conventional manner known in the art. Other methods and/or apparatus known in the art for isolation of nucleic acids from a biological sample, such as olig(dT) cellulose for mRNA isolation, may be utilized as well.

Element 16 represents conventional apparatus and method for amplifying nucleotide sequences in that sample that are delineated by targeted by the primer pairs according to the invention. In a preferred embodiment, element 16 comprises conventional apparatus for performing polymerase chain reaction amplification of the nucleic acids using such primer pairs. Though the illustrated embodiment utilized PCR amplification, those skilled in the art will appreciate that other techniques, e.g., ligation chain reaction or radioactively or flourescently tagged primers, may be used as well for identifying targeted nucleotide sequences in the sample.

Element 18 represents conventional apparatus or methods for separating the amplified fragments produced by element 16. In a preferred embodiment, element 18 comprises conventional gel electrophoresis apparatus. Gel electrophoresis (preferably through polyacrylamide gel) is used to facilitate identification of the physical or chemical properties of the nucleotide regions targeted by the 3',5' primer pairs and, in particular, to identify the length or molecular weight of those regions (as evidenced by bands in the gel). Other properties, such as the existence of such targeted-delineated regions (e.g., as revealed by radioactively or flourescently tagged primers) may be used in alternate embodiments of the invention.

Element 20 represents a video camera used in an automated embodiment of apparatus 10 to generate a digital image of the "output" of element 18, e.g., a digital image of separated fragments for analysis by machine vision software, e.g., in control and analysis unit 22, to determine the aforementioned chemical or physical properties of the delineated regions. In a preferred, non-automated system, those properties are determined in a conventional manner by measuring the distance to and between bands in the electrophoresis gel.

Element 22 represents a digital data processor, e.g., a conventional "personal computer" programmed for operation in accord with the teachings herein, for generating a fingerprint as a function of the property each targeted-delineated nucleotide region as a function of the identity of the 3',5' primer that targeted it. In a preferred embodiment, element 22 generates a fingerprint database 24 representing, for each targeted-delineated region, the identity of the 5',3' primer pair and the distance to the band corresponding to the region on the gel.

In one preferred embodiment, the database 24 is preferably in the form of a 3-dimensional matrix, with 5' primer identity constituting a first index, 3' primer identity constituting a second index, and band length constituting the third index. For example, where the PCR reaction using primer pair 16, 29 (i.e., 5' primer #16, and 3' primer #29) results in an gel bands at 150 and 475 (i.e., representing respective targeted-delineated regions of 150 and 475 nucleotides in length), the database stores two values, one at coordinate 16, 29, 150 and one at coordinate 16, 29, 475. The stored values are preferably a Boolean value 1 (or 0) indicating that existence (or non-existence) of a band associated with the 3',5' primer pair. More preferably, the stored values can represent an intensity of the detected band.

The database or matrix 24 is preferably stored in volatile memory, e.g., RAM, and/or secondary storage, e.g., magnetic disk, for display, analysis or comparison with fingerprints generated for other biological samples. In addition, to being stored in memory, database or matrix 24 can be graphically displayed in the manner shown in FIG. 1 using conventional mathematical graphical packages.

Those skilled in the art will appreciate that the database or matrix 24 can be stored and presented in formats other than the 3-dimensional ones described above. For example, the database can be stored in two dimensional format, with the 5' primer identity representing a first index, the 3' primer identity representing a second index, and the band distances (s) (i.e., length or molecular weight) constituting values stored at those indices. Or, alternatively, the database can be stored in one dimensional format, with a hash (or other function) of the 5' primer and 3' primers representing a single index and the band distances(s) representing the stored values.

Selective Amplification of Nucleotide Sequences

Figure 2:
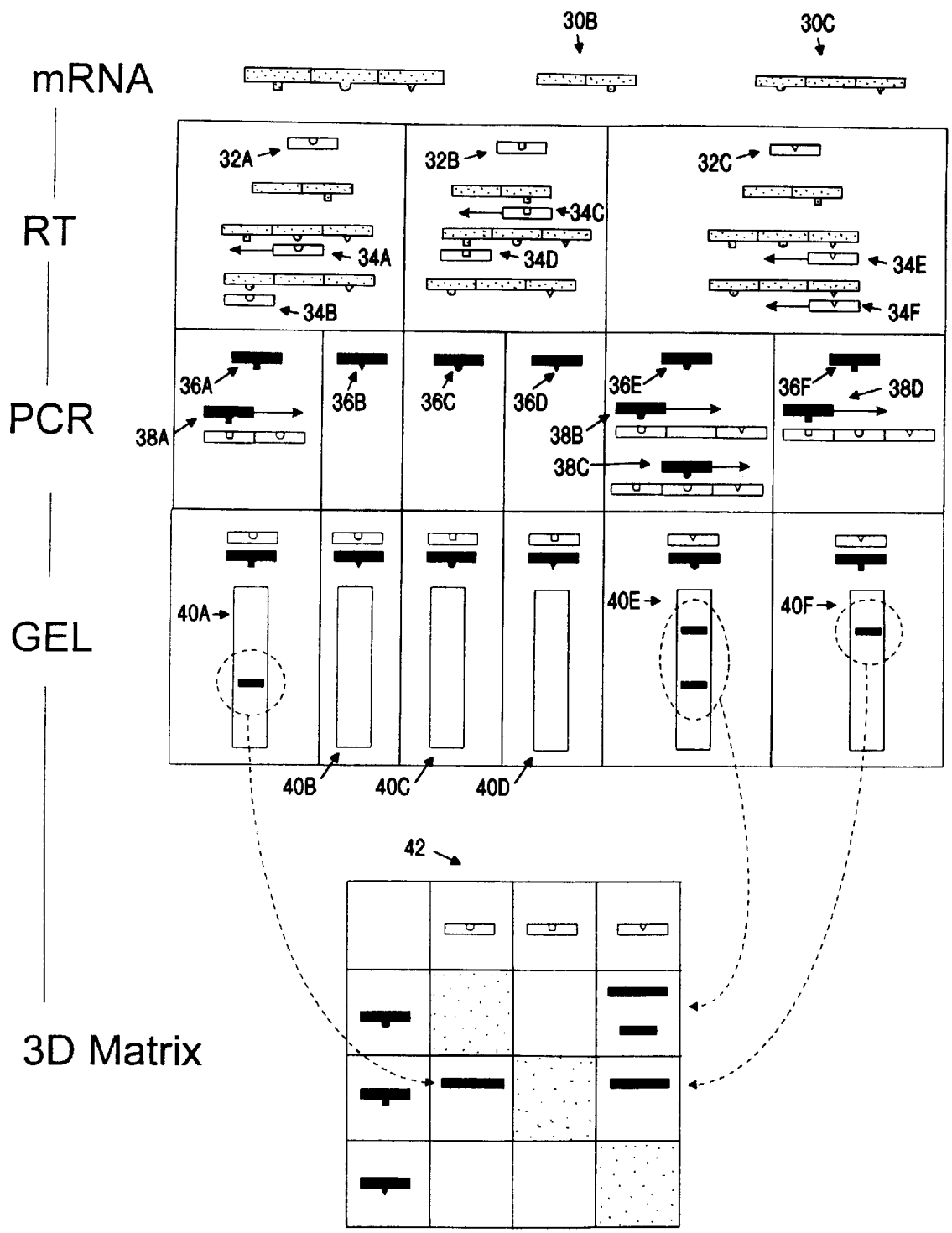
FIG. 2 depicts a mechanism by which reverse transcription and PCR are used, in conjunction with the 3',5' primer pairs according to the invention, to amplify nucleotide sequences delineated by subsequences which hybridize with those pairs.

FIG. 2 depicts a mechanism by which reverse transcription and PCR are used in a preferred embodiment of the invention for characterizing a sample comprising mRNA using 3',5' primers according to the invention.

At the top of the drawing are depictions of three representative mRNA sequences 30A–30C contained in the biological sample to be characterized. Potential primer target sites on the mRNA are represented as square, circular and triangular shapes, each representing a different respective subsequence of one or more nucleotides with which a 3' primer according to the invention may selectively hybridize. Thus, mRNA 30A representatively includes a square, circular and triangular site; mRNA 30B, a square site; and mRNA 30C, a circular and triangular site. It will be appreciated that in an actual sample, there are likely to be far more than three mRNA sequences, that small number being shown here for sake of simplicity.

In a reverse transcription phase of the process, labeled "RT," the sample is divided into portions corresponding to the number of 3' primers. The mRNAs 30A, 30B, 30C in each portion are reverse transcribed using a respective 3' primer 32A, 32B, 32C in the presence of reverse transcriptase. The resulting cDNA are depicted as elements 34A–34F.

In a detection phase, labeled "PCR," each portion is again subdivided into two subportions: one subportion for each 5' primer that is not complementary to the 3' primer used in reverse transcription of the parent portion. A PCR reaction is run on each subportion using the 3' primer of the parent portion and a respective non-complementary 5' primer. Thus, referring to the representative graphical symbols used in the illustration, PCR reactions are run with the "round" 3' primer 32A and each of the "square" and "triangular" 5' primers 36A, 36B; the "square" 3' primer 32B and each of the "round" and "triangular" 5' primers 36C, 36D; and with the "triangular" 3' primer 32C and each of the "round" and "square" 5' primers 36F, 36E.

Nucleotide sequences in each subportion that are flanked or bounded by subsequences to which the 3',5' primer pair hybridize are amplified. Such amplification is shown by cDNA sequences 38A–38D. As shown in the illustration, amplified sequence 38A corresponds to primer pair 32A, 36A; amplified sequence 38D corresponds to primer pair 32C, 36F; and amplified sequences 38B and 38C correspond with primer pair 32C, 36E.

In a phase, labeled "GEL," for determining the properties of the amplified sequences, each subportion is subjected to gel electrophoresis to separate the amplified products. Gels 40A, 40E and 40F show bands corresponding to amplified products 38A–38D, as shown. Gels 40B–40D are bandless, since none of the corresponding PCR reactions resulted in amplified product.

In an indexing phase, labeled "3D Matrix," a matrix 42 is constructed reflecting the properties of the amplified products in the gels 40A–40F. Thus, the molecular weight or length of amplified sequence 38A, as reflected by the distance of the corresponding band in gel 40A, is stored in matrix 42 and indexed by the identity of primer pair 32A, 36A. Amplified sequences 38B–38D are likewise stored in the matrix 42 as indexed by their respective primer pairs. The remaining matrix entries remain empty, since the corresponding primer pairs produced no amplified result in the PCR reaction.

The matrix 42 generated from a candidate sample can be compared with that of a reference sample to determine the relative nucleotide content thereof. A reference matrix, for example, can be generated from a healthy cell line using the procedures and primers hereof. That reference matrix can be compared with the matrix generated from a candidate sample to determine differences in nucleic acid content of the samples. Those skilled in the art will appreciate that such use of reference and candidate sample matrices is valuable, for example, in the identification and diagnosis of disease.

The matrix 42 can be analyzed of its own, e.g., to determine the relative positioning of nucleotides contained in the sample. Thus, for example, for three PCR products—referred to here as "A," "B," and "C"—generated during the detection phase described above, if the following conditions are met:

i) the 5' primer associated with products "A" and "C" are the same, ii) the 3' primer associated with products "B" and "C" are the same, iii) the 3' primer associated with product "A" is complementary to the 5' primer associated with product "B," and iv) the sum of the lengths of products "A" and "B" are substantially equal to the length of product "C" (excluding overlap regions defined by the primers themselves), it is likely that, in the sample, the nucleotide sequence corresponding to product "A" is adjacent to that corresponding to product "B," and that the nucleotide sequence corresponding to product "C" comprises that corresponding to products "A" and "B."

Selection of Primers

Computation of Frequency of Incidence of 6 to 9-Tuples

Figure 3:
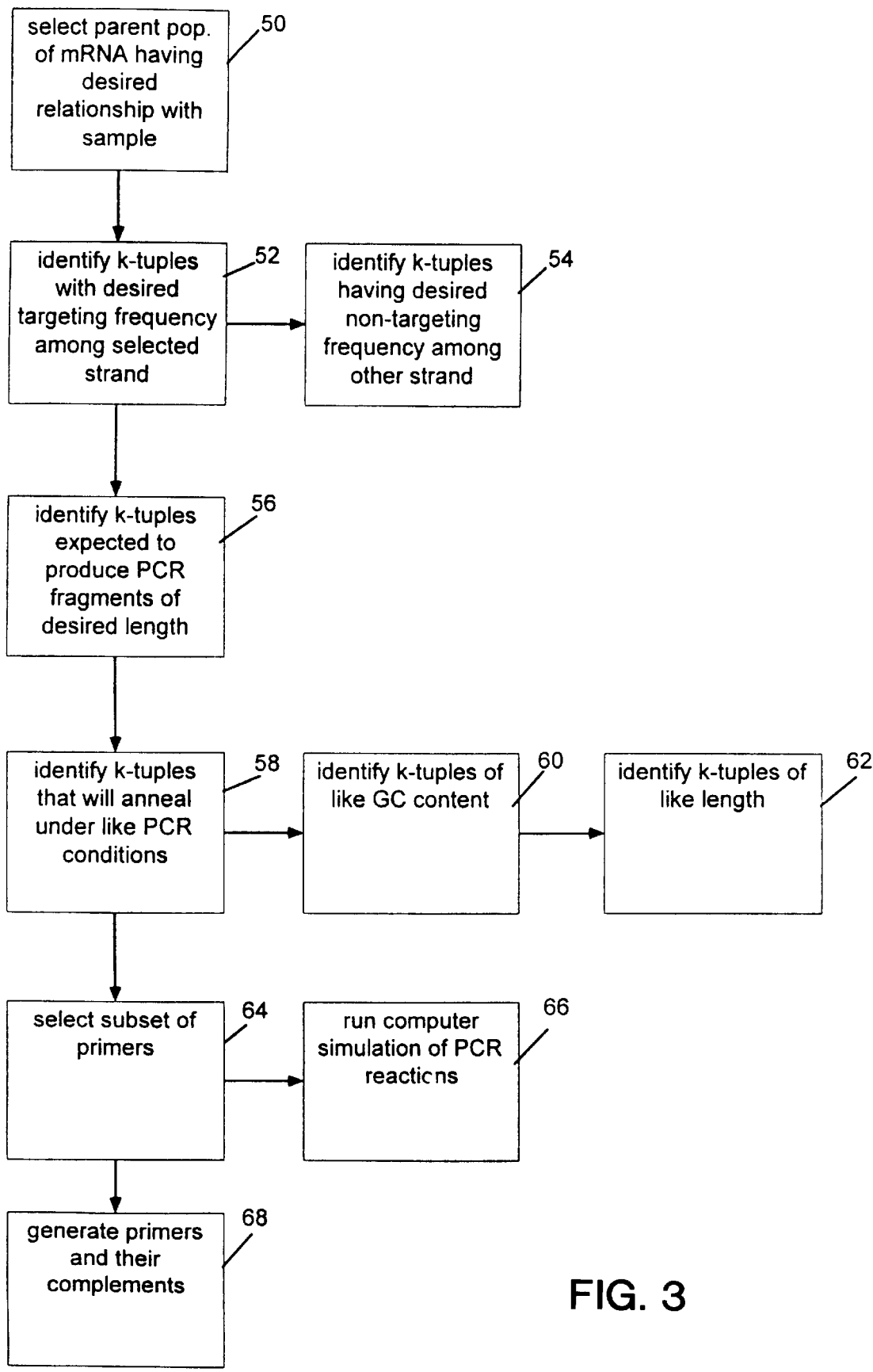
FIG. 3 depicts a preferred methodology for selecting 3' and 5' primers for use in generating a "fingerprint" as shown in FIGS. 1 and 2.

FIG. 3 depicts a preferred methodology for generating a kit of 3',5' primers for use in generating a "fingerprint" as described above. Beginning in step 50, a parent population is selected having a desired relationship with samples to be characterized. In a preferred embodiment for characterizing samples containing human mRNA, one thousand human mRNAs were randomly selected from Entrez: Sequences release 6.0 and 7.0 (National Center for Biotechnology Information) as representative of a parent population of human coding regions.

Nucleotide sequences analyzed from the randomly selected mRNA included enzymes, hormones, growth factors, structural proteins, immunoglobulins, receptors, transporters and other diverse genes. The starting and final positions of coding regions in each mRNA were manually extracted. Human mRNAs with unspecified coding regions, non-specific nucleotide sequences in coding regions, or introns were not included in the statistical analysis.

The frequency of incidence of all 348,160 possible 6 to 9-tuples (hexa to nonanucleotides) in one thousand randomly selected human coding regions was computed for both the sense and antisense strands. Although human genes stored in databases are not truly a random sample of the human genome, they are likely to be an adequate sample for the computation of frequencies of incidence of 6 to 9-tuples. They may serve substantially well, also, for fingerprinting samples of related species, e.g., mouse (see Example 2).

The sense and antisense mRNA frequency (number of mRNAs in which a given k-tuple occurs) of all 6 to 9-tuples was also computed in the one thousand coding regions. This was done because it is important to consider not only the overall frequency of a given k-tuple, but also its gene distribution. A k-tuple that is present 100 times in 100 different genes is more widely distributed than one present 100 times in 5 genes due to repetitive sequences in those genes.

From the foregoing information, a database was created containing the following six fields: sense k-tuple, sense frequency of incidence, sense mRNA frequency, antisense k-tuple, antisense frequency of incidence and antisense mRNA frequency.

Selection of Number of Original Primers and PCR Product Size Range

Our analysis showed that a small subset of k-tuples is shared by a high proportion of all human coding region sense strands. Using this finding, a PCR-based strategy was devised to achieve highly selective screening, isolation and identification of the entire transcriptionally active human genome. A set of PCR primers was designed by pairing sense-selective oligonucleotides (original primers) with the complement of all the other oligonucleotides in the set. Complementary primers are selective for the antisense strands. As those skilled in the art will appreciate, PCR of a combination of a primer and its own complementary oligonucleotide cannot be effectively run due to technical reasons.

As evident in FIG. 2 and the corresponding text, every time two original primers are present in a gene at a distance amenable to PCR a product will be formed. PCR products obtained will be separated in two dimensions, the 5' primer and the 3' primer. If all products formed with an specific 5'-3' primer pair are resolved by size in an electrophoretic gel, a three dimensional (3D) matrix of PCR products results.

The 3D-matrix size should be small enough to be practical and feasible, but large enough to accommodate all mRNAs. It is estimated that 10 to 15 thousand genes are transcriptionally active in a particular cell at any given time. Due to technical reasons, up to 100 PCR products sized between 50 to 600 base pairs can effectively be resolved per sequencing gel. Since the size range is restricted, the number of "cells" in the 3D-matrix will depend primarily on the number of original primers. The number of primer pairs in the a system according to the invention is a square function $(n^2-n)$ of the number of original primers.

The number of original primers was preliminary set at 30. The resulting 870 $(30^2-30)$ primer pairs (5' primer, 3' primer) combined with 550 positions (length 50 to 600) produce a 3D-matrix with 478,500 cells. This 3D-matrix can potentially accommodate up to 87,000 (870×100) PCR products, which will allow an average of 5.8 (87,000/15,000) PCR products per mRNA. The combination of multiple products located in specific locations in these almost half a million cells of the 3D-matrix (3D-fingerprint) will be very specific for any given gene. Thus, 3D-fingerprints can be used to identify thousands of genes simultaneously. The 3D-fingerprints for all known (cloned and sequenced) human genes can be generated by computer simulation as discussed below.

Selection of Original Primers Sense and Antisense Gene Frequencies

In steps 52 and 54 (FIG. 3), a set of potential primers are identified from the aforementioned information gleaned from the parent population. To this end, a first set is identified that will hybridize with k-tuples that occur relatively frequently—i.e., between 5% and 25% and, preferably, between 9% and 21%—in a selected strand, e.g., the antisense strand. A second set is then identified that will hybridize relatively infrequently—i.e., less than 10% and, preferably, less than 5%—with the other strand, e.g., the sense strand. Potential primers reside at the intersection of those sets, i.e., primers that are common to both sets. Preferably, primers that hybridize relatively infrequently with the sense strand are selected directly from the first set, rather than independently identifying the sets and, then, finding their intersection.

In step 56, the set of potential primers is narrowed to include those which, when used in pairs, will result in PCR products of desired length (or molecular weight). This will depend on the resolution of the medium used to detect PCR amplification products. In the preferred illustrated embodiment, that length is between 50 and 600 base pairs. The set of primers pairs that will hybridize with targets to delineate subsequences of such length can be selected independently, with the potential primers being selected from among those present in all sets. Preferably, however, the set of such delineating primers is selected directly from the prior sets.

In a preferred practice for determining primers for characterizing human coding regions, an original primer sense gene frequency (or, in alternate terms, a frequency of occurrence of intentionally targeted k-tuples in the antisense strand) of 15±6% (9 to 21%) was considered to be adequate. If an original primer is present in 15% of human coding region sense strands, a set of 30 of such primers will be present an average of 4.5 times per gene (0.15×30). The theoretical total number of PCR products of any size will be $(n-1)+(n-2)+\ldots+(n-n)$, where n is the number of primer set occurrences per gene. The number of PCR products size 50 to 600 base pairs formed per mRNA will depend not only on the number of occurrences, but also the specific locations of the original primers in those mRNAs.

Figure 4:
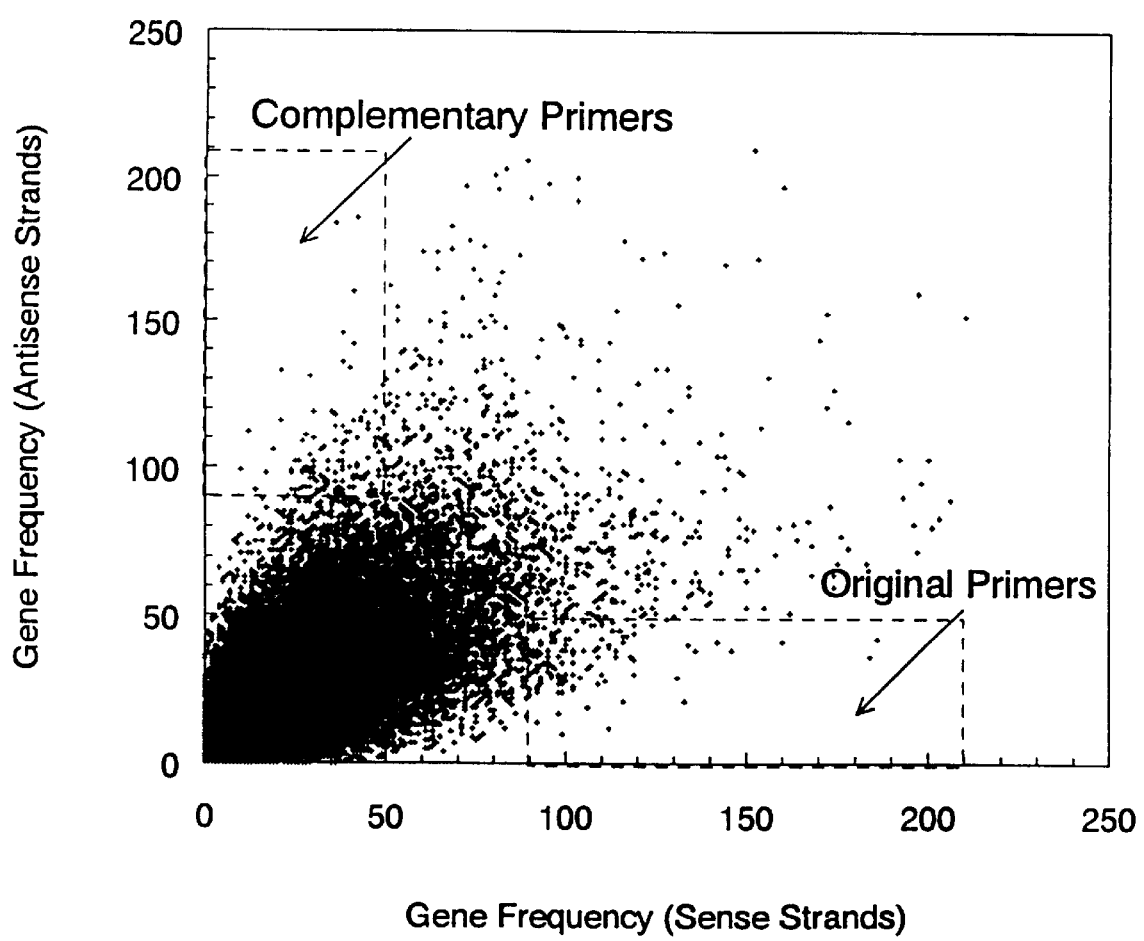
FIG. 4 is an XY plot showing sense and antisense gene frequencies for octanucleotides with GC content 4 or 5 [n=32,256] in 1,000 human coding regions.

Ideally the antisense gene frequency of original primers (or, in alternate terms, a frequency of occurrence of unintentionally targeted nucleotides in the sense strand) should be as low as possible if one wants to generate a set of sense specific primers. However, it was found that primers that are very frequent in the sense strands of coding regions tend also to have a higher frequency in the antisense strands. An XY plot showing the relationship between sense and antisense frequency for octanucleotides with GC content 4 or 5 in 1,000 human coding regions is shown in FIG. 4. An antisense gene frequency of less than 5% was arbitrarily set for original primers.

Those skilled in the art will appreciate that the sense and antisense gene frequencies are exemplary only and that other frequency ranges may prove quite suitable consistent with the teachings herein and in view of the length of the primers, the frequency spectrum of the parent population, the resolution of the electrophoresis gel (or other separating device), among other factors.

As evident in FIG. 2 and the accompanying text, a way to significantly increase the 5' original-3' complementary specificity is to use complementary primers to reverse transcribe mRNAs. There are four possible different ways in which one original and one complementary oligonucleotide can act as primers in a PCR reaction: 5' original-3' complementary, 5' complementary-3' original, 5' original-3' original and 5' complementary-3' complementary. The possibility of original oligonucleotides acting as 3' primers will be virtually eliminated (by the reverse transcription step). Considering the sense strands as templates, original oligonucleotides are statistically more likely to act as 5' primers and their complementary as 3' primers. The only other remaining choice is one complementary oligonucleotide acting both as 5' and 3' primer, but the probability of this event is extremely unlikely. All primer pairs in which the complementary primer is present will form such a product, so it will be immediately recognized.

Length and GC Content of Original Primers

In steps 58–62 (FIG. 3), a set of potential primers is identified which will anneal under like PCR conditions. Preferably, this is determined by identifying subsets that have substantially like GC content, i.e., between 25%–50% or 50%–75%, and targeting portions (that is, portions that hybridize with specific designated nucleotides) of substantially like length, between 5 and 20 nucleotides and, preferably, between 6 and 12 nucleotides and, more preferably, between 7 and 9 nucleotides and, most preferably, of 8 nucleotides. These subsets can be determined independently of the sets described in connection with steps 52 and 54, with the potential primers being selected from among those present in all sets (and subsets). Preferably, however, the set of primers which will anneal under like conditions are selected directly from the prior set.

A similar length and GC content is required for primer pairs to have similar annealing temperatures. Assuming a random distribution, the calculated expected frequency of 30 k-tuples will be 30 divided by the number of different combinations $(30/4^k)$ 6-tuples 1 in 136.5

7-tuples 1 in 546.1

8-tuples 1 in 2,185.5

9-tuples 1 in 8,738.1

Two oligonucleotides from a set of 30 randomly selected 6 or 7-tuples will frequently be less than 600 bps apart and will form PCR products of this size range. On the other hand, this event will be unlikely for a set of 30 randomly selected oligonucleotides of length 8 or 9 due to their lower expected frequency. As previously mentioned, a sense gene frequency of 9 to 21%, and an antisense gene frequency of less than 5% and a similar GC content were preferred for original primers. The number of 9-tuples that fall within specified parameters was insufficient to complete a primer set (estimated number required 30). For these reasons, a length of 8 was preferred for oligonucleotide primers. From all 65,536 possible 8-tuples, 151 had a GC content of 4 or 5 and the selected sense-antisense gene frequencies (see FIG. 4). Given equipment capable of running the necessary number of PCR reactions, these 151 oligonucleotides constitute a preferred set of 5' primers for use in characterizing human (and related) biologic samples. 3' primers can be produced as complementary to these 151 oligonucleotides and combined with the non-complementary 5' primers to form a kit containing $151^2$–151 (or 1361) primer pairs.

A table listing these 151 original oligonucleotides (5' primers) and their complementary oligonucleotides (3' primers) follows:

| 5' PRIMERS | | | | | | |
|---|---|---|---|---|---|---|
| aacctgga | aagaggag | aagcagga | aagctgga | aaggagac | aaggagct | aaggagga |
| aaggaggc | aaggccaa | acaagctg | accagaag | accccaag | accctgga | acctgaag |
| acctgctc | acctggaa | acctggac | acctggag | agaacctg | agaagagc | agaaggac |
| agaaggcc | agaccctg | agacctgg | agaggaga | agaggagc | agatcctg | agatgcag |
| agcctgga | aggacaag | aggagaac | aggccaag | agtggaag | atcctgga | atgaggag |
| atgctgga | caacccca | caacctgg | caagaagc | caagaagg | caagcaga | caagcagc |
| caagctgc | caagctgg | caaggaag | caaggaca | caaggaga | caaggagc | caaggagg |
| caagtgg | caccaaga | caccaagg | cagaagac | cagaagct | catcaagg | catcgtgg |
| catgaagg | ccaagaag | ccaagcag | ccaagctg | ccaaggag | ccagagga | ccagatga |
| ccatcaag | ccctgaag | ccctgatg | cctcacca | cctgaagg | cctgagga | cctggaaa |
| cctggaga | cctggtgt | ctacctgg | ctgacctg | ctgcagaa | ctgccaag | ctggacaa |
| ctggacct | ctggagac | ctggccaa | ctggtgaa | ctgtggaa | ctgtggac | ctgtggag |
| gaacctgg | gaagccaa | gaagctga | gaaggaag | gaaggaca | gaagtgga | gacaagga |
| gacccaga | gaccctga | gacctgct | gacctgga | gagaagag | gagaagct | gagaagga |
| gagctgaa | gaggacct | gaggagat | gaggccaa | gatcctgg | gatgcaga | gatgtgga |
| gcaagaag | gccaagaa | gccaagga | gctgaagc | ggaagaga | ggacaaga | ggagaaag |
| ggagaaca | ggagaacc | ggagaatg | ggagatgc | ggagcaga | ggaggagt | ggccaaga |
| gtggacat | gtggagaa | gtggagac | gtggagct | tacctgga | tcaagcag | tcaaggag |
| tcaccaag | tcaccctg | tccctgga | tcctggac | tctgtgga | tgaccctg | tgaggagg |
| tgctgagc | tgctggac | tggaagtg | tggacaag | tggaccag | tggacctg | tggagaac |
| tggagacc | tggagaga | tggagagc | tggaggac | tggaggct | tggatgag | tggccaag |
| tggtggac | tgtgcctg | tgtggaca | tgtggaga | | | |

-continued

3' PRIMERS

| | | | | | | |
|---|---|---|---|---|---|---|
| acaccagg | actcctcc | agcaggtc | agcctcca | agctccac | agctcctt | agcttctc |
| agcttctg | aggtccag | aggtcctc | atctcctc | atgtccac | cacttcca | cagcttgg |
| cagcttgt | caggatct | caggcaca | cagggtca | cagggtct | cagggtga | caggtcag |
| caggtcca | caggttct | catcaggg | cattctcc | ccaccttg | ccacgatg | ccagcttg |
| ccaggatc | ccaggtag | ccaggtct | ccaggttc | ccaggttg | cctcctca | cctccttg |
| ccttcagg | ccttcatg | ccttcttg | ccttgatg | ccttggtg | ctcatcca | ctccacag |
| ctccaggt | ctcctcat | ctcctctt | ctccttga | ctccttgg | ctcttctc | ctgcatct |
| ctgcttga | ctgcttgg | ctggtcca | cttcaggg | cttcaggt | cttccact | cttccttc |
| cttccttg | cttctggt | cttcttgc | cttcttgg | cttgatgg | cttggcag | cttggcca |
| cttggcct | cttggggt | cttggtga | cttgtcca | cttgtcct | ctttctcc | gagcaggt |
| gcagcttg | gcatctcc | gcctcctt | gctcagca | gctcctct | gctccttg | gctctcca |
| gctcttct | gctgcttg | gcttcagc | gcttcttg | ggccttct | ggtctcca | ggttctcc |
| gtccacag | gtccacca | gtccagca | gtccagga | gtccaggt | gtcctcca | gtccttct |
| gtctccac | gtctccag | gtctcctt | gtcttctg | gttctcca | gttctcct | tcagcttc |
| tcagggtc | tcatctgg | tccacaga | tccacatc | tccacttc | tccagcat | tccagctt |
| tccaggat | tccaggct | tccaggga | tccagggt | tccaggta | tccaggtc | tccaggtt |
| tcctcagg | tcctcctt | tcctctgg | tcctgctt | tccttctc | tccttggc | tccttgtc |
| tctccaca | tctccagg | tctcctct | tctccttg | tctctcca | tctcttcc | tctgcatc |
| tctgctcc | tctgcttg | tctgggtc | tcttggcc | tcttggtg | tcttgtcc | tggggttg |
| tggtgagg | tgtccaca | tgtccttc | tgtccttg | tgttctcc | ttcaccag | ttcagctc |
| ttccacag | ttccaggt | ttctccac | ttctgcag | ttcttggc | ttggccag | ttggcctc |
| ttggcctt | ttggcttc | ttgtccag | tttccagg | | | |

Selection of Final Set of Original Primers

Given the demands of running and tracking 1361 PCR reactions, subsets of the aforementioned 151 primers can be utilized in generating fingerprints. The number of primers will depend on a balance between yield and efficiency of gene detection. The size of that group can range from 1 to 5 primers; 5 to 10 primers; 10 to 30 primers; 30 to 50 primers; or more than 50 primers. As noted above, a preferred set for use in generating a fingerprint includes 30 or the primers; although the smaller subsets can be used, e.g., for differential analysis with respect to such a fingerprint. Selection of a subset, e.g., of 30 primers, from the final candidates is depicted in steps 54 and 56, and is described below.

The number of possible sets of 30 primers from 65,536 possible octanucleotides is $3.1 \times 10^{144}$. By reducing the number of 8-tuples to 151, one still has $1.3 \times 10^{66}$ different combinations of 30 primers. Although ideal, it is not feasible to generate (even by computer simulation) a 3D matrix for each one of these combinations in the representative sample of one thousand human mRNAs.

Therefore, the following steps were taken to identify a subgroup of 30 from the final 151 candidates:

(1) computer simulation of 870 (30×30−30) PCR reactions using statistically designed sense-antisense (original-complementary) primer pairs, (2) computer simulation of separation of the resulting products of 870 PCR reactions in 6% sequencing gels (size range 50 to 600 bps), (3) generation of a 3D matrix (original primer, complementary primer, product size) of all PCR products size 50 to 600 bps (pre-selected size window of the 3D-Link system), (4) computation of number of genes represented in the 3D matrix.

Our approach was to randomly generate multiple sets of 30 primers from the 151 candidate oligonucleotides, and store the number of times each candidate primer was present in combinations that produced a high gene yield based on computer simulation. After an specific candidate primer achieved a predetermined frequency it was fixed as a final primer. After 5.3 million iterations all 30 primers were selected by computer simulation.

Figure 5:
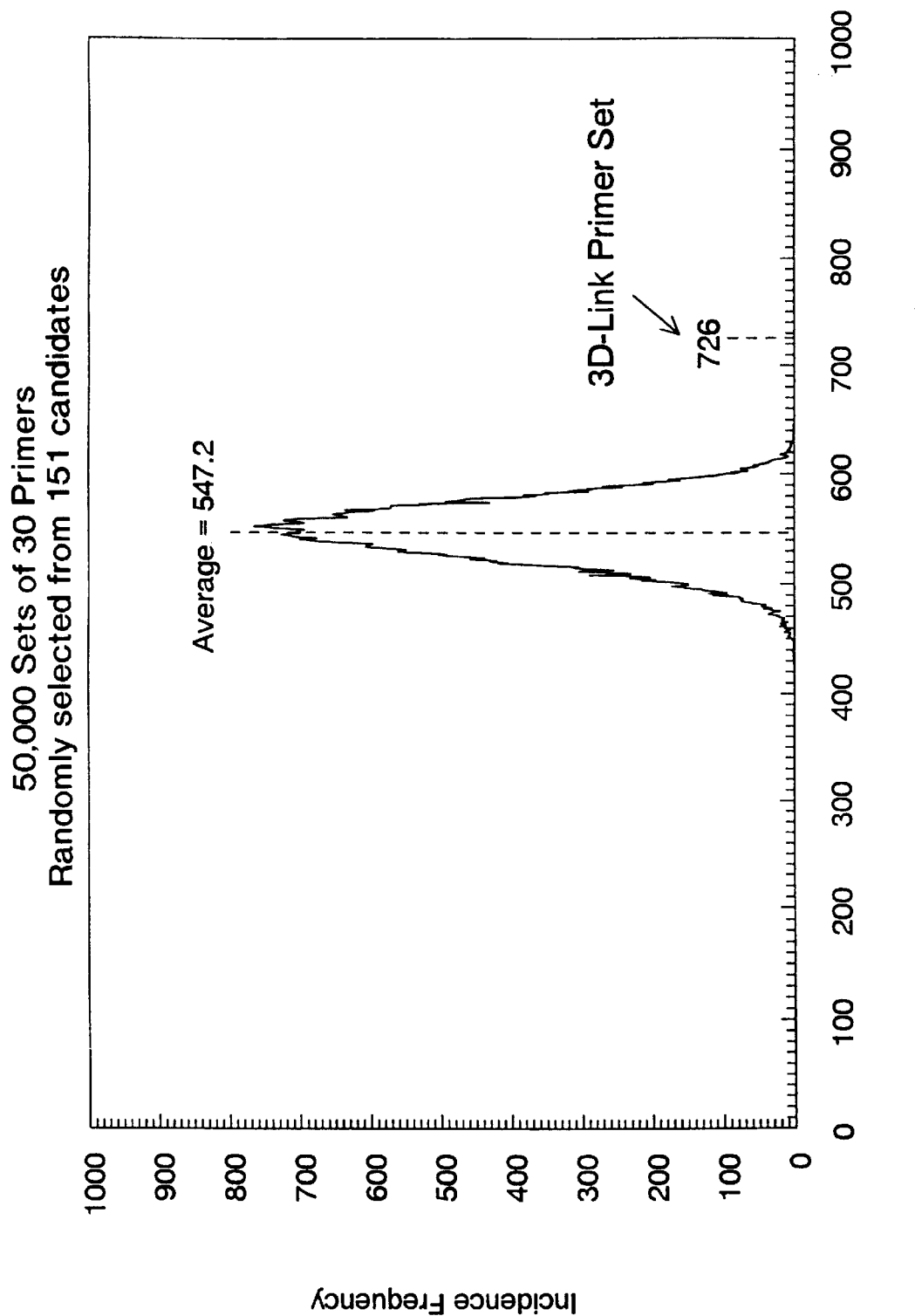
FIG. 5 depicts a number of human coding regions detected by 50,000 sets of 30 primers (original and complementary) randomly selected from 151 oligonucleotides according to the invention. Also shown for comparative purposes are a number of genes detected by a preferred set of 30 primers according to the invention.

FIG. 5 shows the number of human coding regions detected by 50,000 sets of 30 primers randomly selected from the 151 candidate oligonucleotides. The average number of coding regions detected by these primer sets was 547.2. The set of 30 original primers selected by our approach was able to detect 726 out of 1,000 human coding regions. It should be noted that only coding regions were used in the primer selection process, but the detection rate is even higher if entire mRNAs are used as initial sample. A total of 763 out of 1,000 human mRNAs were detected by the selected set of 30 original primers.

The table below shows the 30 preferred primers according to the invention for use in characterizing nucleotide sequences. The table also shows the gene frequency of those primers in both the sense and antisense strand of 1,000 human mRNAs coding regions.

| | Original (5' Primers) | | Sense Strands Gene | | Antisense Strands Gene | | Complementary (3' Primers) | |
|---|---|---|---|---|---|---|---|---|
| No. | GNC Code | Primer | Freq. | Freq. | Freq. | Freq. | GNC Code | Primer |
| 1 | 24,200 | cctggaga | 221 | 186 | 44 | 42 | 56,650 | tctccagg |
| 2 | 34,280 | gacctgga | 188 | 160 | 49 | 41 | 54,445 | tccaggtc |
| 3 | 8,841 | agaggagc | 110 | 102 | 34 | 34 | 40,311 | gctcctct |

-continued

| | Original (5' Primers) | | Sense Strands | | Antisense Strands | | Complementary (3' Primers) | |
|---|---|---|---|---|---|---|---|---|
| No. | GNC Code | Primer | Freq. | Freq. | Freq. | Freq. | GNC Code | Primer |
| 4  | 24,074 | cctgaagg | 135 | 117 | 56 | 49 | 24,394 | ccttcagg |
| 5  | 17,032 | caaggaga | 153 | 133 | 21 | 21 | 56,702 | tctccttg |
| 6  | 20,610 | ccaagaag | 160 | 134 | 40 | 40 | 32,250 | cttcttgg |
| 7  | 35,363 | gaggagat | 153 | 131 | 29 | 29 | 14,173 | atctcctc |
| 8  | 47,648 | gtggagaa | 162 | 142 | 44 | 41 | 63,313 | ttctccac |
| 9  | 33,400 | gaagctga | 133 | 119 | 52 | 47 | 53,885 | tcagcttc |
| 10 | 59,486 | tggacctg | 137 | 119 | 42 | 35 | 19,156 | caggtcca |
| 11 | 8,357  | agaaggcc | 116 | 108 | 49 | 47 | 42,487 | ggccttct |
| 12 | 31,042 | ctgccaag | 110 | 102 | 38 | 37 | 32,402 | cttggcag |
| 13 | 14,824 | atgctgga | 118 | 114 | 39 | 38 | 54,419 | tccagcat |
| 14 | 55,201 | tcctggac | 153 | 128 | 55 | 49 | 46,376 | gtccagga |
| 15 | 21,048 | ccagatga | 118 | 110 | 44 | 42 | 54,138 | tcatctgg |
| 16 | 59,528 | tggagaga | 124 | 104 | 50 | 29 | 56,788 | tctctcca |
| 17 | 23,828 | cctcacca | 99  | 92  | 39 | 38 | 60,298 | tggtgagg |
| 18 | 41,474 | ggagaaag | 125 | 106 | 39 | 32 | 32,629 | ctttctcc |
| 19 | 2,344  | aagcagga | 105 | 96  | 43 | 43 | 55,199 | tcctgctt |
| 20 | 59,458 | tggacaag | 120 | 109 | 27 | 27 | 32,468 | cttgtcca |
| 21 | 19,898 | catcgtgg | 104 | 93  | 27 | 27 | 20,878 | ccacgatg |
| 22 | 24,104 | cctgagga | 131 | 110 | 52 | 47 | 55,114 | tcctcagg |
| 23 | 24,192 | cctggaaa | 114 | 97  | 48 | 44 | 64,842 | ttTccagg |
| 24 | 31,008 | ctgcagaa | 127 | 107 | 55 | 47 | 63,378 | ttctgcag |
| 25 | 8,542  | agacctg  | 125 | 98  | 32 | 30 | 19,127 | cagggtct |
| 26 | 33,512 | gaagtgga | 122 | 108 | 38 | 38 | 54,397 | tccacttc |
| 27 | 29,050 | ctacctgg | 131 | 112 | 12 | 12 | 21,170 | ccaggtag |
| 28 | 59,273 | tgctgagc | 103 | 99  | 52 | 48 | 40,228 | gctcagca |
| 29 | 19,978 | catgaagg | 126 | 113 | 46 | 45 | 24,398 | ccttcatg |
| 30 | 35,296 | gagctgaa | 111 | 95  | 40 | 38 | 62,621 | ttcagctc |

The total frequency of all listed 30 primers is 1 in 412.2 (3,934 in 1,624,764) in the sense strands and 1 in 1,285.0 (1,236 in 1,624,763) in the antisense strands. The expected frequency for thirty 8-mers assuming a random distribution is 1 in 2,184.5 (612.7 in 1,624,763). Thus, the sense frequency of original primers is 5.3 times higher than expected and their antisense frequency is 1.7 times expected. Complementary oligonucleotides have exactly the opposite sense and antisense frequencies. As mentioned before, the sense specificity that can be achieved is limited by a directly proportional relationship between sense and antisense frequency in human coding regions.

The 30 original (5') primers were present 4,515 times in 1,000 human mRNAs (2,298,399 base pairs In computer simulations, the total number of PCR products produced using the processes hereof and the 30 listed primers in one thousand human mRNAs was 5,241. As previously mentioned, the number of mRNAs represented in the 3D matrix was 76.3% (763 out of 1,000).

Figure 6:
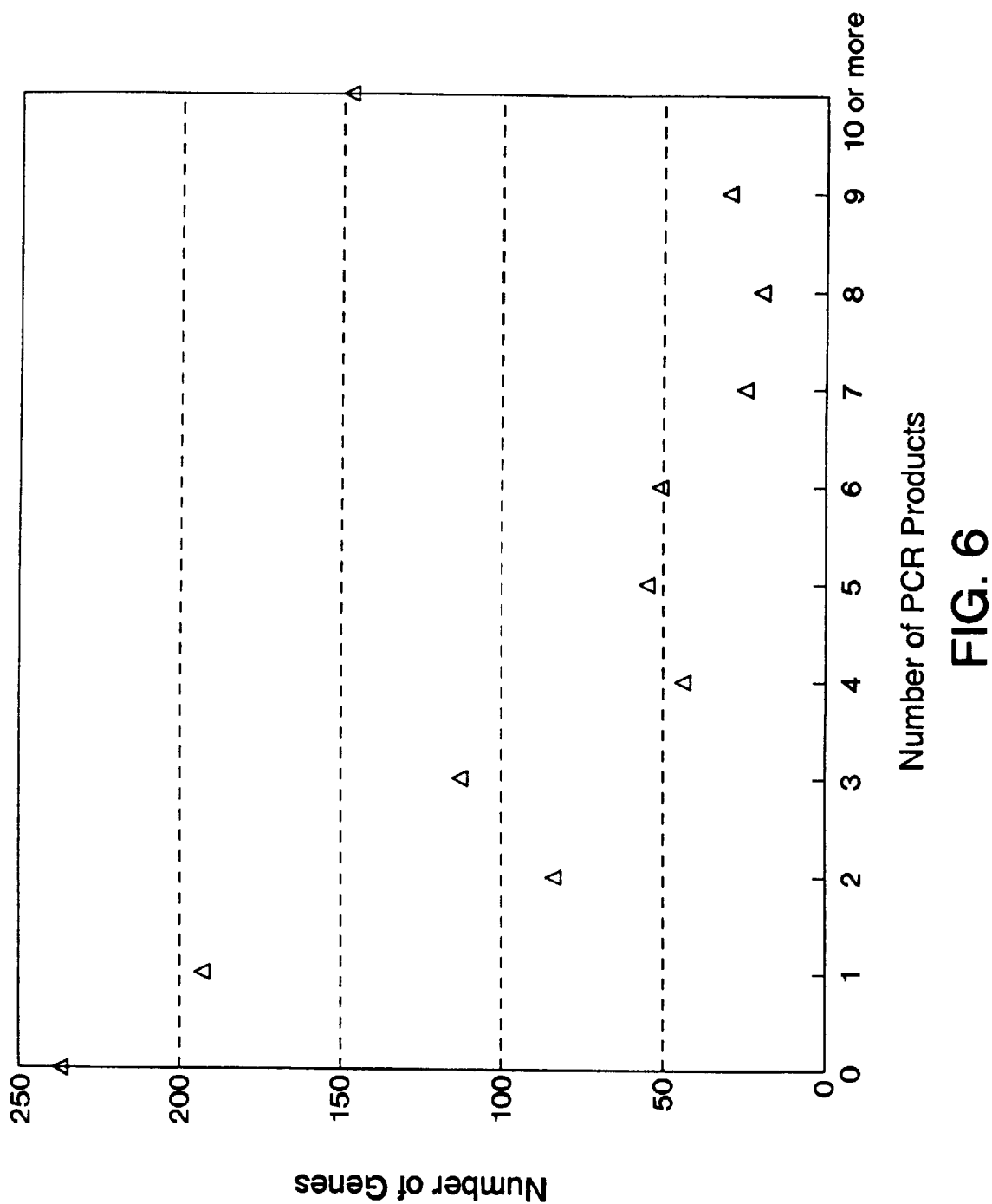
FIGS. 6–8 show a number of PCR products per gene, a distribution of PCR products by length, and a distribution of frequencies of PCR products for a preferred set of 5'–3' primer pairs according to the invention.
Figure 7:
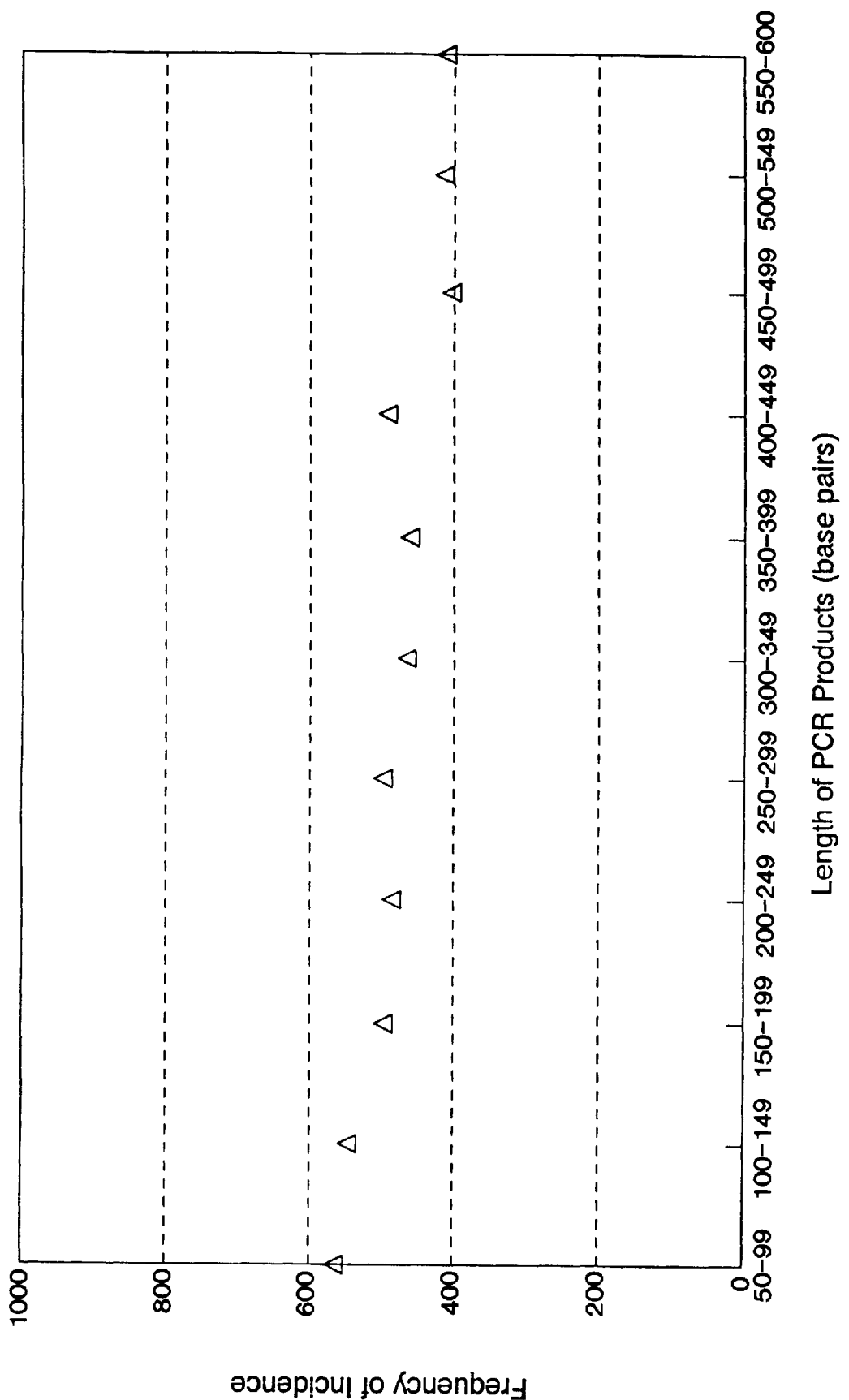
Figure 8:
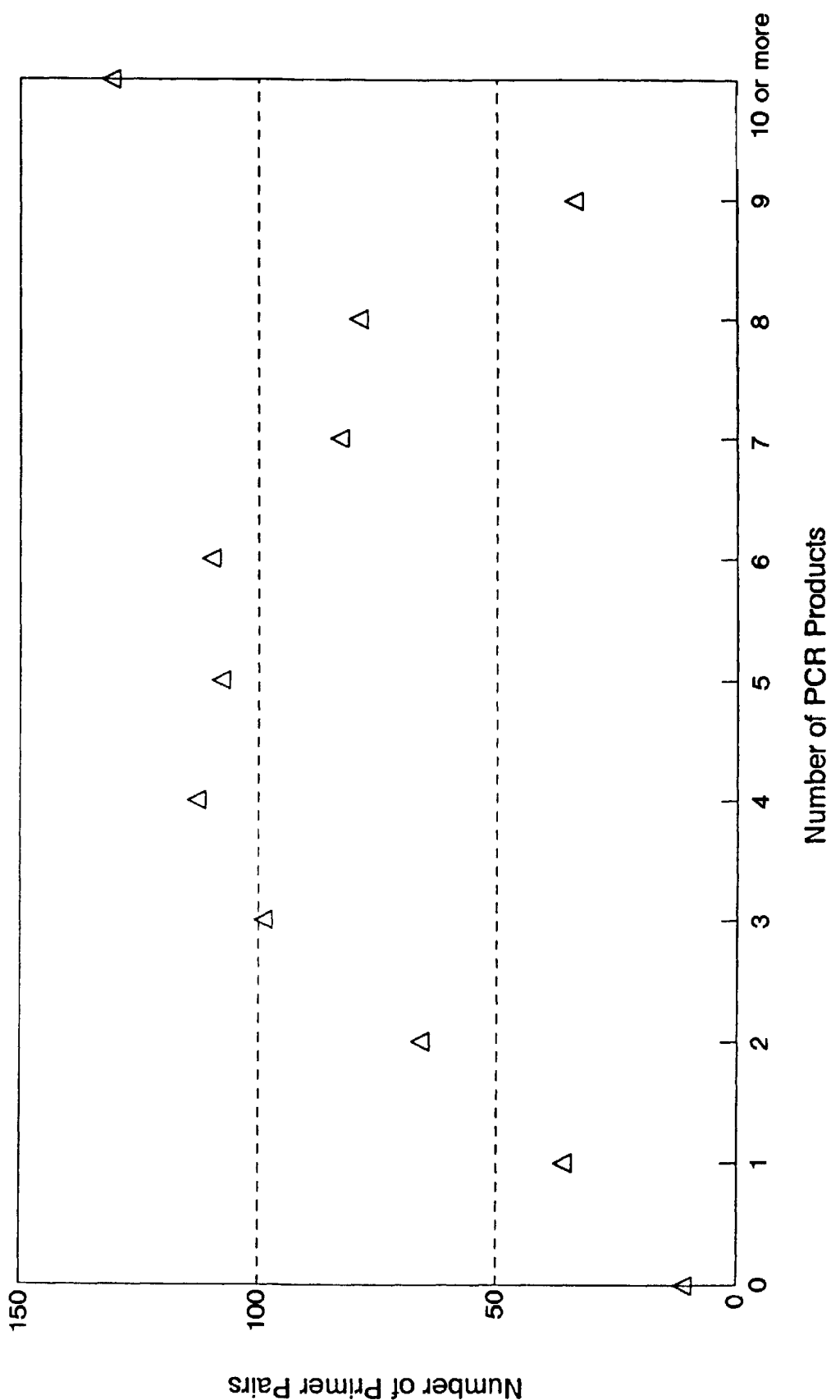

The distribution of frequencies of PCR products formed per mRNA is displayed in FIG. 6. An average of 5.2 PCR products were formed per mRNA (5,241 in 1,000 mRNAs). The number of PCR products per primer pair, for the 30 listed primers, and the distribution of PCR products by length are shown in FIGS. 7 and 8. The results show that cells of the 3D-matrix will be filled by PCR products in a homogeneous way.

Figure 9:
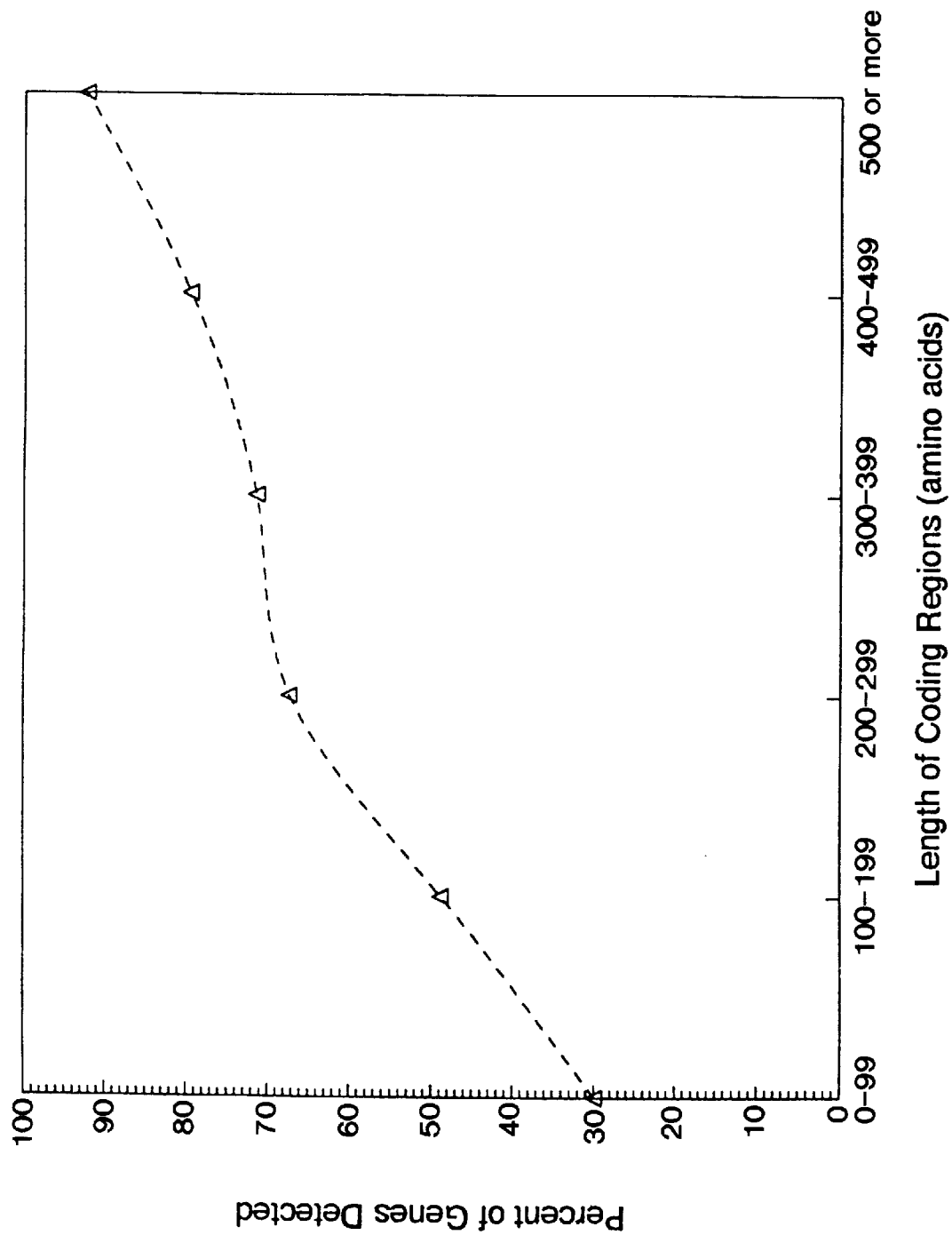
FIG. 9 depicts a relationship between length of the mRNA coding regions and percent of mRNAs detected by processes, apparatus and compositions according to the invention.

The relationship between length of the mRNA coding regions and percent of mRNAs detected by the processes hereof, using the 30 primers listed above, is shown in FIG. 9. The explanation for the observed directly proportional relationship is that the longer the coding region of a mRNA, the higher the probability of two original primers to be located at a distance between 50 and 600 in the mRNA. Coding regions shorter than 100 codons were only detected 30.0% of the time, as oppose to 92.4% detection rate in coding regions longer or equal to 500 codons.

Figure 10:
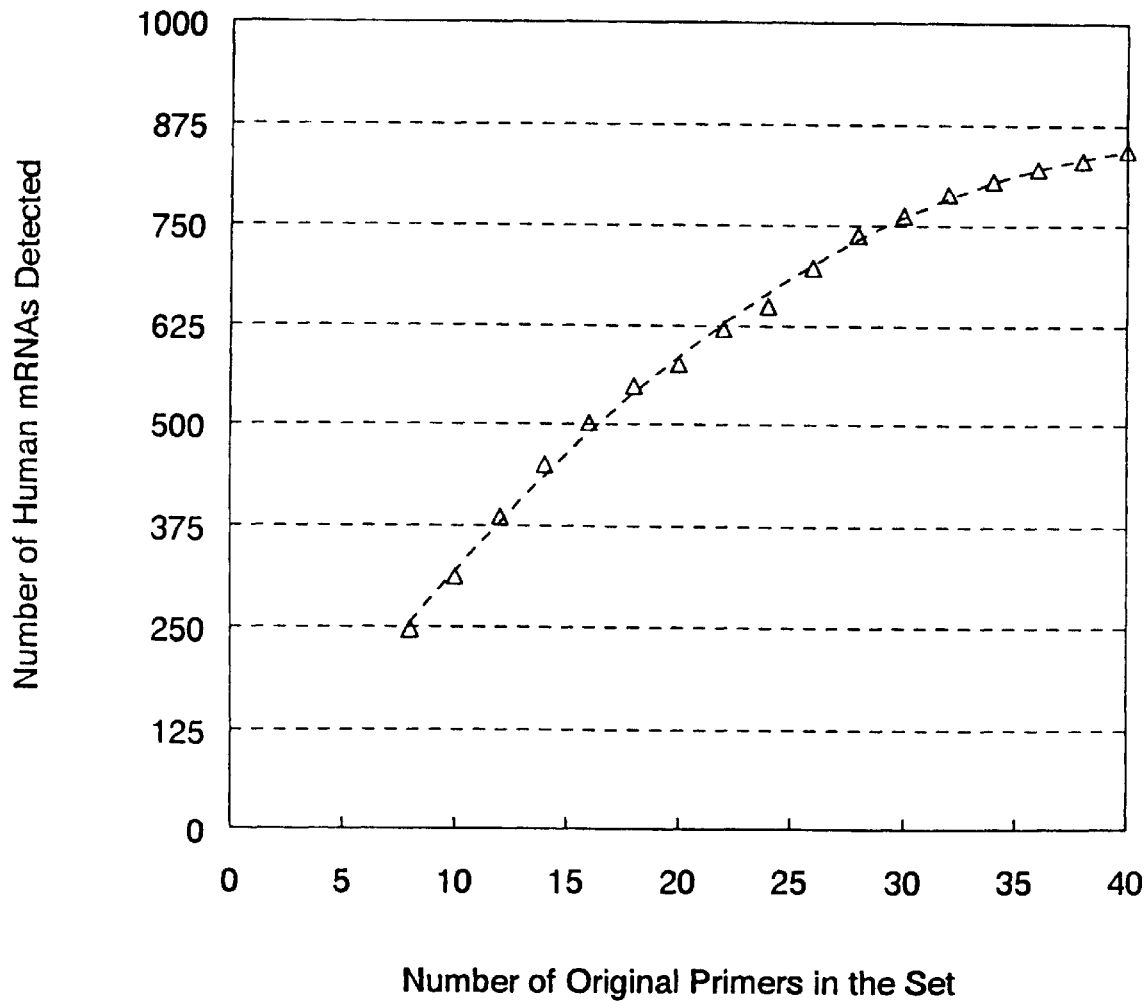
FIG. 10 depicts a relationship between a number of original primers according to the invention and a percent of human mRNAs detected thereby in connection with the processes and apparatus of the invention.

The relationship between the number of original (5') primers and the percent of human mRNAs detected, for the 30 primers listed above, is shown in FIG. 10. As expected, the percent of genes detected increases with the number of original primers. Since the number of primer pairs (PCR reactions) in the 3D-matrix is a square function of the number of original primers, the efficiency of the system decreases as the number of original primers increases. Eight original primers (56 PCR reactions) were able to detect 24.7% of 1,000 human mRNAs. In order to double (50.2%) and triple (75.0%) the number of mRNAs detected, 16 original primers (240 PCR reactions) and 29 original primers (812 PCR reactions) were necessary. Increasing the number of original primers to 40 (1,560 PCR reactions) only increased by 10% (84.5%) the percentage of mRNAs detected.

EXAMPLE 1

Simulation with One Hundred Randomly Selected Human mRNAs

Reverse transcription and PCR reactions as described above in connection with FIG. 2 were simulated by computer with the set of 30 original and 30 complementary primers listed above in one hundred randomly selected human mRNAs different from the aforementioned one thousand mRNAs. The original primers were present 434 times in the sense strands of the 100 mRNAs (214,396 base pairs). The number of PCR products formed was 515, and the number of genes detected was 73% (73 out of 100). These results suggest that the processes, apparatus and compositions hereof have general applicability to the entire transcriptionally active human genome.

EXAMPLE 2

Simulated Comparison of the 3D-Link Primer Set With a Randomly Generated "Primer Set" in Human, Mouse, Drosophila, Yeast and Randomly Generated "Sequences"

Figure 11:
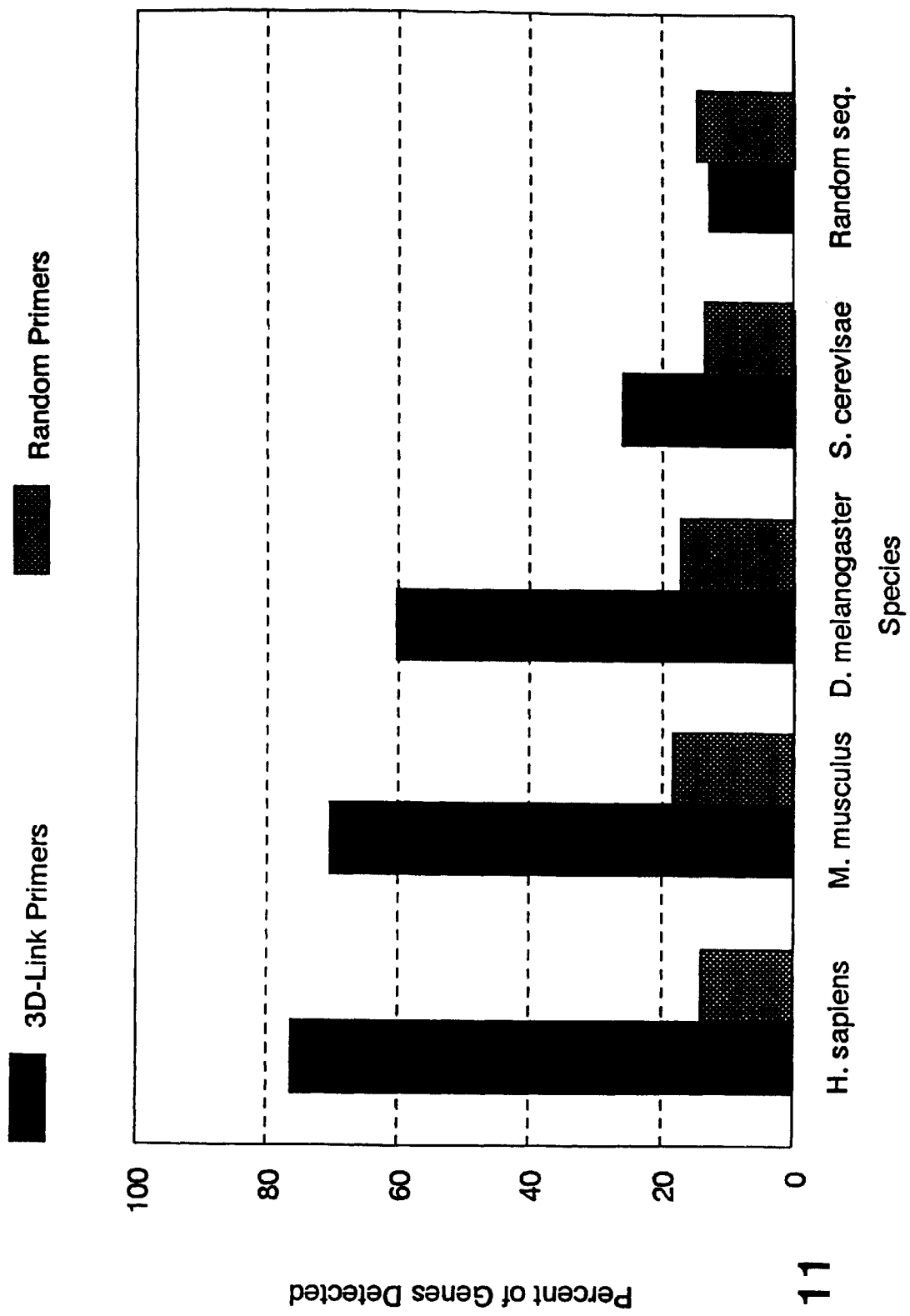
FIG. 11 depicts a percent of genes detected in *H. sapiens, M. musculus, D. melanogaster, S. cerevisae,* as well as in a randomly generated sequence, using a preferred primer set of 30 original and complementary primers according to the invention. The figure also depicts a percent of genes detected by a randomly selected set of octanucleotide primers.

FIG. 11 shows the percent of genes detected in *H. sapiens* (n=1,000), *M. musculus* (n=250), *D. melanogaster* (n=250), *S. cerevisae* (n=250) and randomly generated sequences (n=1,000), using the 3D-Link primer set (30 original and complementary primers) and an equivalent randomly selected set of octanucleotide primers. Computer simulations involving random primers and sequences were done as experimental controls. A fingerprint matrix was generated with 30 random octanucleotides in 1,000 human mRNAs (2,298,399 base pairs), the 30 above-cited original primers in 1,000 strings of randomly generated sequence of matching length, and 30 random 8-mers in 1,000 strings of random sequence. The number of PCR products were 203, 215 and 224, respectively, a 23-fold reduction compared to 5,241 products formed by the 3-Link primer set in 1,000 human mRNAs. The number of genes detected was reduced 5-fold (14.1%, 12.9% and 14.7% compared to 76.3%). The computer simulations in mouse, drosophila and yeast were done in order to explore the potential utility of the human 3D-Link to characterize nucleic acids of other species. The results obtained indicate that the human 3D-Link system serves substantially well for fingerprinting samples of related species (mouse 70.4%, drosophila 60.4%). Results obtained in more distant species are not very different from random controls (yeast 26%). It should be noted that the lack of selectivity for yeast genes can be advantageous if the 3D-Link system is used to fingerprint YACs containing DNA from human or related species.

EXAMPLE 3

Using mRNAs From a Human Hepatic Cell Line
Cell Culture and RNA Isolation

A human hepatic cell line (Hep G2passage 16) was cultured in Eagle's minimum essential medium (Sigma) with 10% FBS. Cells were frozen after 3 days of growth. RNA was isolated using centrifugation through cesium chloride (5.7 M) and guanidine thiocyanate (4 M) as has been previously described. RNA obtained was washed with 20 mls of sodium acetate (3 M, pH 5.2), 200 mls of DEPC water and 513 mls of absolute ethanol (final concentration 70%), and stored at −86° C. for one hour. The mRNA was then washed two times with 70% ethanol and vacuum spinned for 30 minutes. The resulting lyophilized RNA was re dissolved in 75 $\mu$l of DEPC water. The quality of the RNA was verified using an agarose gel. The concentration (determined by absorbance at 260 mm) was 1.93 $\mu$g/$\mu$l.

Reverse Transcription and PCR Amplification of Human mRNAs

Five original and five complementary of the aforementioned primers were obtained from Oligos Etc. Short oligonucleotides are known to prime in a degenerate fashion in the 5' end. Therefore, we added four inosines to the 5' end of all designed octanucleotides (8-tuples) to allow specific priming in the eight bases located in the 3' end. Due to the lower coupling efficiency of inosines, all oligonucleotides were purified by HPLC.

The human RNA obtained from Hep G2 cells was reverse transcribed using designed antisense oligonucleotide primers. M-MLV reverse transcriptase was obtained from Gibco BRL. Assay conditions were as recommended by the manufacturer (2 $\mu$g RNA, 10 mM DTT, 3 mM $MgCl_2$, 75 mM KCl, 50 mM Tris-HCl, 2.5 $\mu$M primer, 0.5 mM of each dNTP and 10 units/$\mu$l of M-MLV).

Using statistically designed sense-antisense (original-complementary) primer pairs, reverse transcribed mRNAs were amplified by the polymerase chain reaction (PCR). The conditions for amplification were modified (to obtained optimum product yield) as follows 1.4 mM MgC12, 50 mM KCI, 13.5 mM Tris-HCI, 50 $\mu$M dNTPs, 0.5 $\mu$M [35 S] dATP, 1 $\mu$M of each oligonucleotide primer and 0.01 units/$\mu$l of Taq DNA polymerase (Perkin Elmer). The annealing temperature was set to 42° C. and the number of cycles was increased to 40.

Gel Separation of PCR Products Obtained with 3D-Link Original-Complementary Primer Pairs The resulting PCR products were separated in 6% polyacrilamide sequencing gels (National Diagnostics). Gels were dried and exposed to scientific imaging film (Kodak) during 72 hours. As predicted, multiple bands were obtained with the statistically designed sense-antisense (original-complementary) primer pairs.

EXAMPLE 4

Mammalian G-Protein Coupled Receptor 3D-Link

The processes, apparatus and compositions described herein can be applied for "fingerprinting" mammalian G-protein coupled receptors (as well as human protein-coding regions, as described above). To this end, 157 coding regions representative of mammalian G-protein coupled receptors were analyzed in the manner described above. Accession numbers of those coding regions follow:

| | | | | |
|---|---|---|---|---|
| D00634 | D10197 | D10204 | D10849 | D10891 |
| D13321 | D90348 | D90402 | D90456 | J02960 |
| J03019 | J03025 | J03823 | J03853 | J04192 |
| J05097 | J05189 | J05276 | J05426 | J05652 |
| L01119 | L03380 | L04473 | L04535 | L04672 |
| L04962 | L09230 | L12398 | M13150 | M16404 |
| M16405 | M16406 | M16407 | M16409 | M21410 |
| M22926 | M23533 | M26199 | M29525 | M29932 |
| M29957 | M30625 | M31210 | M31774 | M31838 |
| M32061 | M32701 | M34041 | M34842 | M35077 |
| M57414 | M58316 | M59967 | M60626 | M60654 |
| M60786 | M61000 | M61099 | M62424 | M62505 |
| M63108 | M64299 | M64749 | M64799 | M65085 |
| M67439 | M68932 | M69118 | M73481 | M73482 |
| M73969 | M74054 | M74290 | M74716 | M76673 |
| M77184 | M80333 | M80436 | M80612 | M81310 |
| M81778 | M81829 | M81830 | M81831 | M81832 |
| M83180 | M84009 | M84562 | M84605 | M85151 |
| M86261 | M86835 | M87834 | M88096 | M88461 |
| M88714 | M89473 | M89953 | M89954 | M89955 |
| M90518 | M91000 | M91466 | M91467 | M93273 |
| M94152 | M96674 | M96738 | M97370 | M97516 |
| M97759 | M97797 | S57565 | X03804 | X04413 |
| X04708 | X06295 | X12712 | X13556 | X13971 |
| X14048 | X14049 | X14051 | X14052 | X15263 |
| X15266 | X17607 | X51585 | X53944 | X54937 |
| X55674 | X55760 | X55812 | X56736 | X57764 |
| X57765 | X57830 | X59132 | X60438 | X61496 |
| X62294 | X62933 | X63574 | X64630 | X64878 |
| X65633 | X65634 | X65635 | X66842 | X67126 |
| X70070 | Z11162 | Z11504 | Z11687 | Z11690 |
| Z14224 | Z18278 | | | |

As explained previously, based on preselected sense/antisense gene frequencies, 121 decanucleotides were chosen as candidate primers:

| | | | | |
|---|---|---|---|---|
| aaccccatca | acatcctggt | accaactact | accatgtaca | accccatcat |
| accgctacct | acctggccat | actacttcct | atcatctgct | atctactcca |
| atctgctggc | caacagctgc | caaccccatc | caacctggcc | caactacttc |
| caccaactac | catcatctac | catcctcaac | catcctcttc | catcctggcc |
| catcctggtg | catctactcc | catctccatc | catctccttc | catctgctgg |
| ccaactactt | ccatcatcta | cccatcatct | ccccatcatc | cctcatctac |
| cctctgctgg | cctgctggcc | cctggaccgc | cctggccatc | ccttcatcct |
| ccttctacct | ccttcttcat | ctacctggcc | ctacttcctg | ctctgctggc |
| ctcttctggc | ctgcccttct | ctgctgctca | ctgctggctg | ctggaccgct |
| ctggccatcg | ctggccctgg | ctggccgtgg | ctggccttca | ctggctgccc |
| ctggctgggc | ctggctgtgg | ctgggctact | cttcatcatc | cttcatcctc |
| cttcatcctg | cttcatcgtg | cttcctgctg | cttcctggtg | gacaggtaca |
| gaccgctacc | gaccgctact | gcatcatcat | gccattgctg | gcccttcttc |
| gcctggcctg | gccttcatca | gccttcatcc | gctatgccaa | gctgcccttc |
| gctgctgctc | gctgctgctg | gctggccttc | gctggctgcc | gctgggctac |
| gctggtcatc | ggaccgctac | ggccttcatc | ggctgcccta | ggctgccctt |
| ggctgggcta | gggctactgg | ggtgctgcc | gtcaccaact | gtctacctgg |
| gtgctggtgt | gtggaccgct | tcaacagcac | tcaaccccat | tcaacctggc |
| tcatcagctt | tcatcatggg | tcatcctcac | tcatctacac | tcatctactg |
| tcatctcctt | tcatctgctg | tcctgctggc | tcctggtggc | tccttcatcc |
| tctacctggc | tctgctggct | tctgggtggc | tgaacctggc | tgaccgctac |
| tgcccttctt | tgctcatcat | tgctgctcat | tgctgctgct | tgctggctgc |
| tgctggtcat | tgctggttcc | tggaccgcta | tggccatcgc | tggccatcgt |
| tggctgccct | tggctgggct | tgggctactg | tggtggctgt | ttcatcatca |
| ttcatcatct | | | | |

Again, as previously described, based on their overall combined ability to detect mammalian G-protein coupled receptors (using computer simulation of the fingerprinting process), 20 original primers (380 primer pairs) were selected as the final primer set:

| | | | | |
|---|---|---|---|---|
| caaccccatc | catcctggtg | catctccatc | cctggccatc | ccttcatcct |
| cttcctgctg | gacaggtaca | gcctggcctg | gctatgccaa | gctgctgctg |
| gctggctgcc | gctgggctac | ggaccgctac | ggccttcatc | tcctg(c,g)tggc |
| tctgctggct | tctgggtggc | tgctcatcat | tgctg(c,g)tcat | tggtggctgt |

Those skilled in the art will appreciate that a corresponding set of 3' primers can be derived from the 5' primers listed immediately above using a like method as that described above in connection with the others sets of of 5' and 3' primers.

This primer set is able to detect 77.7% (122 out of 157) of the mammalian G-coupled protein receptors analyzed. The average number of PCR products per gene was 3.2 (496 PCR products from 157 genes). Diverse G-protein coupled receptors were identified, including muscarinic (1,2,3,4,5), alpha (1b,1c,1d,2a,2b,2c) and beta (1,2,3) adrenergic, adenosine (1,2a,2b,3), histamine (1,2), dopamine (1,2,3,4, 5), tachykinins (nk1,2,3), somatostatin (1,2,3,4), bombesin (1,2), 5-HT (1a,1b,1d), endothelin (a,b) bradykinin (1), FPR (1,2), glucagon, MGLUR (1,4), PTH, ACTH, MSH, TSH, FSH, LH/HCG, GNRH, oxytoxin, vasopressin (1a), neuropeptide Y, neurotensin, prostanoids (EP3 alpha and beta), VIP, CCK (a,b), IL8R (a,b), C5a, PAF, opioid, canabinoid, and orphan receptors (R334, EDG1, RCD1, G10D).

Exemplary Embodiment

The steps of one exemplary preferred embodiment combining the processes listed above for producing a kit of primers and characterizing nucleotide sequences are as follows:

(1) Selection of subset of genetic information that will be probed (e.g. coding regions of human mRNAs)
(2) Statistical analysis of all known (cloned and sequenced) genes within the selected subset, in order to obtain the distribution of frequencies of all k-tuples and their complementary oligonucleotides (done using coding regions from 1,000 randomly selected human mRNAs)
(3) Identification of k-tuples specific for the coding region sense strand of the selected genetic subset with similar length and GC content (e.g., 151 oligonucleotides of length 8 bps, a GC content of 4 or 5, and a sense gene frequency>9% and <21% and an antisense gene frequency of less than 5% were found—see FIG. 4).
(4) Computer simulation of the fingerprinting process (e.g., reverse transcription and PCR-based amplification) using random combinations of the selected oligonucleotides, in order to find a primer set with a high gene yield (e.g., multiple sets of 30 primers were generated using the original 151 candidate oligonucleotides and their ability to detect genes compared—see FIG. 5).
(5) Design a set of PCR primer pairs, by combining original primers with each one, except its own, complementary oligonucleotide.
(6) Run PCR with these primer pairs.
(7) Resolve products by size in electrophoretic gels.
(8) Generation of a 3D-matrix (5' primer, 3' primer, size) by locating in their respective "cells" all PCR products obtained with each primer pair combination.

Advantages

The novel processes, apparatus and compositions described herein are advantageously used in the identification of nucleotide sequences for the following reasons:

1) The presence of multiple products located in specific cells of the 3D-matrix ("3D-fingerprint") is likely to be very specific for a particular gene and can be used for positive identification of thousands of genes simultaneously without use of sequencing, mapping or hybridization techniques.

2) A system according to the invention as described is designed to selectively target specific genomic subsets (e.g. human protein-coding regions) based on their overall nucleotide composition. Our technique can use as initial sample virtually any type of nucleic acids (e.g. human mRNA; human DNA contained in vectors, cosmids, YACs, etc.). Previous methods (e.g. DD-PCR) that target a nucleotide sequence restricted to a type or class of nucleic acids (e.g. the polyA tail of mRNAs) are non-specific and can only be used to characterize that class of nucleic acids (e.g. mRNAs).

3) Using mRNAs as starting material, a 3D-matrix of the transcriptionally active human genome can be generated. Linkage analysis in this "virtual map" of the genome will allow functional bonds between genes to be examined, in a manner analogous to the way physical proximity is tested in physical maps. Genes that are regulated by the same transcription factors, hormones, growth factors, or other specific modulators during cell differentiation will be present simultaneously in the matrix with a higher frequency than non-functionally related genes.

4) The human fingerprint can be very useful to scientists searching for disease genes. This functional map will be more efficient for gene detection than even a detailed physical map of the human genome (the final objective of the Human Genome Project).

5) The products amplified are isolated as bands in electrophoretic gels. Thus, these products can be eluted from the bands, reamplified and sequenced. Used in this fashion the 3D-matrix can be considered a catalogue of already isolated transcriptionally active coding regions.

6) The 3D-fingerprints of all known and sequenced human genes can be predicted by computer simulation of the technique in genes stored in databases (GenBank, EMBO). This will allow potential identification of thousands of genomic fingerprints before they are actually generated.

SUMMARY

Described above are novel processes, apparatus and compositions for characterizing nucleotide sequences in a biological sample. Those processes, apparatus and compositions meet the objects by providing improved capabilities for mapping of genomic DNA, the identification and isolation of nucleotide sequences, the understanding of functional relationships between such sequences, and the diagnosis of disease. These and other objects are evident in the discussion that follows.

Those skilled in the art will appreciate that the embodiments described above are exemplary and that modifications within the ken of those of ordinary skill in the art fall within the scope of the claimed invention. Such modifications are noted in the text above by way of example.

In view of the foregoing, what we claim is:

What is claimed is:

1. A process for characterizing one or more nucleotide sequences in a sample, each such sequence comprising one or more nucleotides, wherein each sequence is characterized by said process comprising the steps of
- A) contacting each nucleotide sequence in said sample, or respective portions thereof, with a plurality of primer pairs, each pair consisting of:
  - (i) a statistically selected K-tuple 5'-primer for hybridizing with relative high frequency to a respective nucleotide subsequence, a complementary subsequence thereto, putatively present in said sample, and
  - (ii) a statistically selected K-tuple 3'-primer for hybridizing with relative high frequency to a different respective nucleotide subsequence, or complementary subsequence thereto, putatively present in said sample, and
- B) detecting regions of said nucleotide sequences in said sample which are delineated by subsequences hybridized with each primer pair,
- C) determining a physical characteristic of each such detected region, and
- D) indexing the physical characteristic of at least one such detected region by an identity of each primer pair that hybridized to its delineating subsequences.

2. A process according to claim 1, wherein step (B) comprises: amplifying said regions of said nucleotide sequences, or complementary sequences thereto, in said sample which are delineated by subsequences hybridized with each primer pair.

3. A process according to claim 2, wherein
- step (A) includes contacting said sample, or respective portions thereof, with a plurality of primer pairs, each of which includes, in addition to said 5' primer, a 3' primer for hybridizing to a downstream nucleotide subsequence, or complementary subsequence thereto, which 3' primer is complementary to a 5' prier of a respective other one of said plural primer pairs,
- step (B) includes performing said amplifying step by polymerase chain reaction (PCR).

4. A process according to claim 3, wherein step (A) includes the steps of selecting said 5' primers to comprise oligonucleotide sequences that
- (i) hybridize, with high frequency, to an antisense strand expected to be amplified by PCR, but
- (ii) hybridize, with relative low frequency, to a sense strand expected to be amplified by PCR.

5. A process according to claim 4, wherein step (A) includes the steps of selecting said 5' primers to have respective targeting portions for hybridizing with specific nucleotide subsequences, said targeting portions comprising oligonucleotides selected from the group of oligonucleotides consisting of aacctgga, aagaggag, aagcagga, aagctgga, aaggagac, aaggagct, aaggagga, aaggaggc, aaggccaa, acaagctg, accagaag, accccaag, accctgga, acctgaag, acctgctc, acctggaa, acctggac, acctggag, agaacctg, agaagagc, agaaggac, agaaggcc, agaccctg, agacctgg, agaggaga, agaggagc, agatcctg, agatgcag, agcctgga, aggacaag, aggagaac, aggccaag, agtggaag, atcctgga, atgaggag, atgctgga, caacccca, caacctgg, caagaagc, caagaagg, caagcaga, caagcagc, caagctgc, caagctgg, caaggaag, caaggaca, caaggaga, caaggagc, caaggagg, caaggtgg, caccaaga, caccaagg, cagaagac, cagaagct, catcaagg, catcgtgg, catgaagg, ccaagaag, ccaagcag, ccaagctg, ccaaggag, ccagagga, ccagatga, ccatcaag, ccctgaag, ccctgatg, cctcacca, cctgaagg, cctgagga, cctgaaa, cctggaga, cctggtgt, ctacctgg, ctgacctg, ctgcagaa, ctgccaag, ctggacaa, ctggacct, ctggagac, ctggccaa, ctggtgaa, ctgtggaa, ctgtggac, ctgtggag, gaacctgg, gaagccaa, gaagctga, gaaggaag, gaaggaca, gaagtgga, gacaagga, gacccaga, gaccctga, gacctgct, gacctgga, gagaagag, gagaagct, gagaagga, gagctgaa, gaggacct, gaggagat, gaggccaa, gatcctgg, gatgcaga, gatgtgga, gcaagaag, gccaagaa, gccaagga, gctgaagc, ggaagaga, ggacaaga, ggagaaag, ggagaaca, ggagaacc, ggagaatg, ggagatgc, ggagcaga, ggaggagt, ggccaaga, gtggacat, gtggagaa, gtggagac, gtggagct, tacctgga, tcaagcag, tcaaggag, tcaccaag, tcaccctg, tccctgga, tcctggac, tctgtgga, tgacctg, tgaggagg, tgctgagc, tgctggac, tggaagtg, tggacaag, tggaccag, tggacctg, tggagaac, tggagacc, tggagaga, tggagagc, tggaggac, tggaggct, tggatgag, tggccaag, tggtggac, tgtgcctg, tgtggaca, and tgtggaga.

6. A process according to claim 4, wherein said sample comprises one or more messenger ribonucleic acid (mRNA) sequences, comprising pre-treating said sample to produce complementary deoxyribonucleic acid sequences (cDNA).

7. A process according to claim 6, wherein said pre-treating step includes the steps of
- contacting each portion of said sample with a 3' primer from a respective one of said plurality of primer pairs, and elongating those 3' primers hybridized to the mRNA in such portion of said sample to form cDNA sequences complementary thereto.

8. A process according to claim 1, wherein step (C) includes determining any of a molecular weight and length of each said detected region.

9. A process according to claim 8, wherein step (C) includes determining a physical characteristic of said detected regions by gel electrophoresis.

10. A process according to claim 8, wherein said indexing step includes the step of generating a matrix representing any of a molecular weight and length of each said detected region, as indexed by the identity of the primer pair that hybridized to its delineating subsequences.

11. An apparatus for characterizing one or more nucleotide sequences in a sample, said apparatus comprising
- A) targeting means for contacting each nucleotide sequence in said sample, or respective portions thereof, with a plurality of primer pairs, each pair consisting of:
  - (i) a statistically selected K-tuple 5'-primer for hybridizing with relative high frequency to a respective nucleotide subsequence, or a complementary subsequence thereto, putatively present in said sample, and (ii) a statistically selected K-tuple 3'-primer for hybridizing with relative high frequency to a different respective nucleotide subsequence, or complementary nucleotide sequence thereto, putatively present in said sample, and B) means for detecting regions of said nucleotide sequences in said sample which are delineated by subsequences hybridized with each primer pair, C) means for determining a physical characteristic of each such detected region, and D) means for indexing the physical characteristic of at least one such detected region by an identity of the primer pair that hybridized to its delineating subsequences.

12. An apparatus according to claim 11, wherein said detecting means comprises means for amplifying said regions of said nucleotide sequences, or complementary sequences thereto, in said sample which are delineated by subsequences hybridized to each primer pair.

13. An apparatus according to claim 12, wherein said contacting means includes means for contacting said sample, or respective portions thereof, with a plurality of primer pairs, each of which includes, in addition to said 5' primer, a 3' primer for hybridizing to a downstream nucleotide subsequence, or complementary subsequence thereto, which 3' primer is complementary to a 5' primer of a respective other one of said plural primer pairs, said detecting means includes means for performing said amplification by polymerase chain reaction (PCR).

14. An apparatus according to claim 13, wherein said sample comprises one or more messenger ribonucleic acid (mRNA) sequences, comprising means for pre-treating each portion of said sample to produce complimentary deoxyribonucleic acid sequences (cDNA).

15. An apparatus according to claim 14, comprising means for pre-treating includes means for contacting each portion of said sample with a 3' primer from a respective one of said plurality of primer pairs, and means for elongating those 3' primers hybridized to the mRNA in such portion of said sample to form cDNA sequences complementary thereto.

16. An apparatus according to claim 11, wherein said determining means includes means for determining any of a molecular weight and length of each said detected region.

17. An apparatus according to claim 16, wherein said indexing means includes means for generating a matrix representing any of a molecular weight and length of each said detected region, as indexed by the identity of the primer pair that hybridized to its delineating subsequences.

18. A kit of primers for use in characterizing one or more nucleotide sequences, wherein said primers are between 5 and 20 nucleotides said kit being produced by a process comprising A) identifying a first set of statistically selected K-tuple primers that hybridize with a relative high frequency of about 5% to about 25%, to respective antisense subsequences putatively present in a nucleotide sequence, or complementary sequence thereto, of said sample, B) identifying a second set of statistically selected K-tuple primers that hybridize, with a relative low frequency of about less than 10%, to respective sense subsequences putatively present in a nucleotide sequence, or a complementary sequence thereto, of said sample, C) providing, as said kit of primers, at least selected primers common to said first and said second sets, said primers being referred to as 5' primers.

19. A kit according to claim 18, produced by a process comprising identifying a third set of plural primers, pairs of which hybridize with relative high frequency to respective pairs of antisense subsequences putatively present in a nucleotide sequence, or complementary sequence thereto, of said sample, which respective pairs of antisense strand subsequences delineate nucleotide sequence regions having a quantifiable physical characteristic falling within a selected range, wherein step (C) includes providing, in said kit of primers, at least selected primers common to said first, second and said third sets.

20. A kit according to claim 19, produced by a process comprising identifying a third set of plural primers, pairs of which hybridize with relative high frequency to respective pairs of antisense subsequences putatively present in a nucleotide sequence, or complementary sequence thereto, in said sample, which respective pairs of antisense strand subsequences delineate nucleotide sequence regions having any of molecular weights and lengths resolvable by a detection apparatus, wherein step (C) includes providing, in said kit of primers, at least selected primers common to said first, second and third sets.

21. A kit according to claim 19, produced by a process comprising identifying a third set of plural primers, pairs of which hybridize with relative high frequency to respective pairs of antisense subsequences putatively present in a nucleotide sequence, or complementary sequence thereto, in said sample, which respective pairs of antisense strand subsequences delineate nucleotide sequence regions having any of molecular weights and lengths resolvable by gel electrophoresis, wherein step (C) includes providing, in said kit of primers, at least selected primers common to said first, second and third sets.

22. A kit according to claim 19, produced by a process comprising identifying a third set of plural primers, pairs of which hybridize with relative high frequency to respective pairs of antisense subsequences putatively present in a nucleotide sequence, or complementary sequence thereto, in said sample, which respective pairs of antisense strand subsequences delineate nucleotide sequence regions having lengths substantially between 50 and 600 base pairs, wherein step (C) includes providing, in said kit of primers, at least selected primers common to said first, second and third sets.

23. A kit according to claim 18, produced by a process comprising identifying a third set of primers that anneal under substantially similar conditions of a polymerase chain reaction, wherein step (C) includes providing, in said kit of primers, at least selected primers common to said first, second and third sets.

24. A kit according to claim 23, produced by a process comprising identifying a fourth set of primers that have substantially like GC content, wherein step (C) includes providing, in said kit of primers, at least selected primers common to said first, second, third sets and fourth sets.

25. A kit according to claim 24, produced by a process comprising identifying as fourth set, primers that have GC content substantially between 50% and 75% or, alternatively, substantially between 25% and 50%.

26. A kit according to claim 23, produced by a process comprising identifying a fourth set of primers that have respective targeting portions for hybridizing with specific nucleotide subsequences, which portions include substantially like numbers of nucleotides, wherein step (C) includes providing, in said kit of primers, at least selected primers common to said first, second, third and fourth sets.

27. A kit according to claim 26, produced by a process comprising identifying, as said fourth set of primers, primers that have targeting portions of length of substantially 8 nucleotides.

28. A kit according to claim 18, produced by a process comprising identifying a third set of plural primers, pairs of which hybridize with relative high frequency to respective pairs of antisense subsequences putatively present in a nucleotide sequence, or complementary sequence thereto, in said sample, which respective pairs of antisense strand subsequences delineate nucleotide sequence regions having any of molecular weights and lengths resolvable by a detection apparatus, identifying a fourth set of primers that have substantially like GC content, identifying a fifth set of primers that have respective targeting portions for hybridizing with specific nucleotide subsequences, which portions include substantially like numbers of nucleotides, wherein step (C) includes providing, in said kit of primers, at least selected primers common to said first, second, third, fourth and fifth sets.

29. A kit according to claim 18, produced by a process wherein step (C) includes selecting primers from said second set for inclusion in said kit by comparison of an expected selectivity of groups within both of said first and second sets.

30. A kit according to claim 29, wherein said kit includes (m) primers and (n) primers are common to both first and second sets, and wherein (m) is less than (n), said kit produced by a process wherein step (C) includes randomly selecting groups of (m) primers from said second set, determining regions of nucleotide sequences, in a sample of known nucleotide sequences, that would be delineated by nucleotide subsequences hybridized to each pair of primers in each such randomly selected group, selecting, for inclusion in said kit, a candidate group of (m) primers that most frequently hybridized to a nucleotide subsequence delineating such regions.

31. A kit according to claim 30, including selecting, as said sample of known nucleotide sequences, a sample representative of known human coding regions.

32. A kit according to claim 30, produced by a process comprising determining a number of regions of nucleotide sequences, in a sample of known nucleotide sequences, that would be delineated by nucleotide subsequences hybridized to each pair of primers in said candidate group of (m) primers, determining a number of regions of nucleotide sequences, in a sample of known nucleotide sequences, that would be delineated by nucleotide subsequences hybridized to each pair of primers in successive groups of (m) primers, each such successive group of (m) primers comprising said candidate group with a respective primer of said second set substituted therein, said successive primer being one not otherwise included in said candidate group of (m) primers, responding to a number of regions delineated by nucleotide subsequences hybridized to each pair of primers in said candidate group being less than a number of regions delineated by nucleotide subsequences hybridized to each pair of primers in a successive group for selecting that successive group as the candidate group.

33. A kit according to claim 18, produced by a process of selecting said 5' primers to have respective targeting portions for hybridizing with specific nucleotide subsequences, said targeting portions comprising a selected plurality of oligonucleotides selected from the group of oligonucleotides consisting of aacctgga, aagaggag, aagcagga, aagctgga, aaggagac, aaggagct, aaggagga, aaggaggc, aaggccaa, acaagctg, accagaag, accccaag, accctgga, acctgaag, acctgctc, acctggaa, acctggac, acctggag, agaacctg, agaagagc, agaaggac, agaaggcc, agaccctg, agacctgg, agaggaga, agaggagc, agatcctg, agatgcag, agcctgga, aggacaag, aggagaac, aggccaag, agtggaag, atcctgga, atgaggag, atgctgga, caacccca, caacctgg, caagaagc, caagaagg, caagcaga, caagcagc, caagctgc, caagctgg, caaggaag, caaggaca, caaggaga, caaggagc, caaggagg, caaggtgg, caccaaga, caccaagg, cagaagac, cagaagct, catcaagg, catcgtgg, catgaagg, ccaagaag, ccaagcag, ccaagctg, ccaaggag, ccagagga, ccagatga, ccatcaag, ccctgaag, ccctgatg, cctcacca, cctgaagg, cctgagga, cctggaaa, cctggaga, cctggtgt, ctacctgg, ctgacctg, ctgcagaa, ctgccaag, ctggacaa, ctggacct, ctggagac, ctggccaa, ctggtgaa, ctgtggaa, ctgtggac, ctgtggag, gaacctgg, gaagccaa, gaagctga, gaaggaag, gaaggaca, gaagtgga, gacaagga, gacccaga, gaccctga, gacctgct, gacctgga, gagaagag, gagaagct, gagaagga, gagctgaa, gaggacct, gaggagat, gaggccaa, gatcctgg, gatgcaga, gatgtgga, gcaagaag, gccaagaa, gccaagga, gctgaagc, ggaagaga, ggacaaga, ggagaaag, ggagaaca, ggagaacc, ggagaatg, ggagatgc, ggagcaga, ggaggagt, ggccaaga, gtggacat, gtggagaa, gtggagac, gtggagct, tacctgga, tcaagcag, tcaaggag, tcaccaag, tcaccctg, tccctgga, tcctggac, tctgtgga, tgaccctg, tgaggagg, tgctgagc, tgctggac, tggaagtg, tggacaag, tggaccag, tggacctg, tggagaac, tggagacc, tggagaga, tggagagc, tggaggac, tggaggct, tggatgag, tggccaag, tggtggac, tgtgcctg, tgtggaca, and tgtggaga.

34. A kit according to claim 33, produced by a process wherein step (C) includes providing, in said kit of primers, a plurality of pairs of primers, each said pair comprising
(i) a respective one of said 5' primers, and
(ii) a complementary primer of each other 5' primer, said complementary primer being referred to as a 3' primer.

35. A kit of primers for use in characterizing a sample comprising one or more nucleotide sequences, each such sequence comprising one or more nucleotides, said kit comprising primers having targeting portions for hybridizing with specific respective nucleotide subsequences, said targeting portions comprising a selected plurality of oligonucleotides selected from the group of oligonucleotides consisting of aacctgga, aagaggag, aagcagga, aagctgga, aaggagac, aaggagct, aaggagga, aaggaggc, aaggccaa, acaagctg, accagaag, accccaag, accctgga, acctgaag, acctgctc, acctggaa, acctggac, acctggag, agaacctg, agaagagc, agaaggac, agaaggcc, agaccctg, agacctgg, agaggaga, agaggagc, agatcctg, agatgcag, agcctgga, aggacaag, aggagaac, aggccaag, agtggaag, atcctgga, atgaggag, atgctgga, caacccca, caacctgg, caagaagc, caagaagg, caagcaga, caagcagc, caagctgc, caagctgg, caaggaag, caaggaca, caaggaga, caaggagc, caaggagg, caaggtgg, caccaaga, caccaagg, cagaagac, cagaagct, catcaagg, catcgtgg, catgaagg, ccaagaag, ccaagcag, ccaagctg, ccaaggag, ccagagga, ccagatga, ccatcaag, ccctgaag, ccctgatg, cctcacca, cctgaagg, cctgagga, cctggaaa, cctggaga, cctggtgt, ctacctgg, ctgacctg, ctgcagaa, ctgccaag, ctggacaa, ctggacct, ctggagac, ctggccaa, ctggtgaa, ctgtggaa, ctgtggac, ctgtggag, gaacctgg, gaagccaa, gaagctga, gaaggaag, gaaggaca, gaagtgga, gacaagga, gaccagga, gaccctga, gacctgct, gacctgga, gagaagag, gagaagct, gagaagga, gagctgaa, gaggacct, gaggagat, gaggccaa, gatcctgg, gatgcaga, gatgtgga, gcaagaag, gccaagaa, gccaagga, gctgaagc, ggaagaga, ggacaaga, ggagaaag, ggagaaca, ggagaacc, ggagaatg, ggagatgc, ggagcaga, ggaggagt, ggccaaga, gtggacat, gtggagaa, gtggagac, gtggagct, tacctgga, tcaagcag, tcaaggag, tcaccaag, tcaccctg, tccctgga, tcctggac, tctgtgga, tggacctg, tgaggagg, tgctgagc, tgctggac, tggaagtg, tggacaag, tggaccag, tggacctg, tggagaac, tggagacc, tggagaga, tggagagc, tggaggac, tggaggct, tggatgag, tggccaag, tggtggac, tgtgcctg, tgtggaca, and tgtggaga.

36. A kit according to claim 35, wherein said selected plurality includes between 2 and 5 of said group of oligonucleotides.

37. A kit according to claim 35, wherein said selected plurality includes between 5 and 10 of said group of oligonucleotides.

38. A kit according to claim 35, wherein said selected plurality includes between 10 and 30 of said group of oligonucleotides.

39. A kit according to claim 35, wherein said selected plurality includes between 30 and 50 of said group of oligonucleotides.

40. A kit according to claim 35, wherein said selected plurality includes more than 50 of said group of oligonucleotides.

41. A kit of primers according to claim 35 comprising primers having targeting portions for hybridizing with specific respective nucleotide subsequences, said targeting portions comprising a selected plurality of oligonucleotides selected from the group of oligonucleotides consisting of aagcagga, agaaggcc, agaccctg, agaggagc, atgctgga, caaggaga, catcgtgg, catgaagg, ccaagaag, ccagatga, cctcacca, cctgaagg, cctgagga, cctggaaa, cctggaga, ctacctgg, ctgcagaa, ctgccaag, gaagctga, gaagtgga, gacctgga, gagctgaa, gaggagat, ggagaaag, gtggagaa, tcctggac, tgctgagc, tggacaag, tggacctg, and tggagaga.

42. A kit of primers according to claim 41, comprising a plurality of pairs of of said primers, each said pair comprising
(i) a respective one of said 5' primers, and
(ii) a complementary primer of each other 5' primer, said complementary primer being referred to as a 3' primer.

43. A process according to claim 1, comprising the step of comparing said indexing of physical characteristics of said candidate sample with an indexing of physical characteristics of a reference sample to determine relative nucleotide content of said candidate and reference samples.

44. A process according to claim 1, comprising the step of analyzing said indexing of physical characteristics of said candidate sample to determine nucleotide content thereof.

45. A process according to claim 44, comprising the step of analyzing said indexing of physical characteristics of plural detected regions, each delineated by subsequences hybridized by a respective primer pair, to determine a relative positioning of nucleotides in said sample.

46. A process according to claim 4, wherein step (A) includes the steps of selecting said 5' primers to have respective targeting portions for hybridizing with specific nucleotide subsequences, said targeting portions comprising decanucleotides selected from the group of decanucleotides consisting of aacccatca, acatcctggt, accaactact, accatgtaca, accccatcat, accgctacct, acctggccat, actacttcct, atcatctgct, atctactcca, atctgctggc, caacagctgc, caacccatc, caacctggcc, caactacttc, caccaactac, catcatctac, catcctcaac, catcctcttc, catcctggcc, catcctggtc, catcctggcc, catcctggtg, catctactcc, catctccatc, catctccttc, catctgctgg, ccaactactt, ccatcatcta, cccatcatct, ccccatcatc, cctcatctac, cctctgctgg, cctgctggcc, cctggaccgc, cctggccatc, cctggccatc, ccttcatcct, ccttctacct, ccttcttcat, ctacctggcc, cctcttcctg, ctctgctggc, ctcttctggc, ctgcccttct, ccgctgctca, ctgctggctg, ctggaccgct, ctggccatcg, ctggccctgg, ctggccgtgg, ctggccttca, ctggctgccc, ctggctgggc, ctggctgtgg, ctgggctact, cttcatcatc, cttcatcctc, cttcatcctg, cttcatcgtg, cttcctgctg, cttcctggtg, gacaggtaca, gaccgctacc, gaccgctaat, gcatcatcat, gccattgctg, gcccttcttc, gcctggcctg, gccttcatca, gccttcatcc, gctatgccaa, gctgcccttc, gctgctgctc, gctgctgctg, gctggccttc, gctggctgcc, gctgggctac, gctggtcatc, ggaccgctac, ggccttcatc, ggctgcccta, ggctgcccctt, ggctgggcta, gggctactgg, ggtgctgccc, gtcaccaact, gtctacctgg, gtgctggtgt, gtggaccgct, tcaacagcac, tcaaccccat, tcaacctggc, tcatcagctt, tcatcatggg, tcatcctcac, tcatctacac, tcatctactg, tcatctcctt, tcatctgctg, tcctgctggc, tcctggtggc, tccttcatcc, tctacctggc, tctgctggct, tctgggtggc, tgaacctggc, tgaccgctac, tgcccttctt, tgctcatcat, tgctgctcat, tgctgctgct, tgctggctgt, tgctggtcat, tgctggttcc, tggaccgcta, tggccatcgc, tggccatcgt, tggctgccct, tggctgggct, tgggctactg, tggtggctgt, ttcatcatca, and ttcatcatct.

47. A kit according to claim 18, produced by a process of selecting said 5' primers to have respective targeting portions for hybridizing with specific nucleotide subsequences, said targeting portions comprising decanucleotides selected from the group of decanucleotides consisting of aacccatca, acatcctggt, accaactact, accatgtaca, accccatcat, accgctacct, acctggccat, actacttcct, atcatctgct, atctactcca, atctgctggc, caacagctgc, caacccatc, caacctggcc, caactacttc, caccaactac, catcatctac, catcctcaac, catcctcttc, catcctggcc, catcctggtg, catctactcc, catctccatc, catctccttc, catctgctgg, ccaactactt, ccatcatcta, cccatcatct, ccccatcatc, cctcatctac, cctctgctgg, cctgctggcc, cctggaccgc, cctggccatc, ccttcatcct, ccttccacct, ccttcttcat, ctacctggcc, ctacttcctg, ctctgctggc, ctcttccggc, ctgcccttct, ctgctgctca, ctgctggctg, ctggaccgct, ctggccatcg, ctggccctgg, ctggccgtgg, ctggccttca, ctggctgccc, ctggctgggc, ctggctgtgg, ctgggctact, cttcatcatc, cttcatcctc, cttcatcctg, cttcatcgtg, cttcctggtg, gacaggtaca, gaccgctacc, gaccgctact, gcatcatcat, gccattgctg, gcccttcttc, gcctggcctg, gccttcatca, gccttcatcc, gctatgccaa, gctgcccttc, gctgctgctc, gctgctgctg, gctggcctcc, gctggctgcc, gctgggctac, gctggtcatc, ggaccgctac, ggccttcatc, ggctgcccta, ggctgcccctt, ggctgggcta, gggctactgg, ggtgctgccc, gtcaccaact, gtctacctgg, gtgctggtgt, gtggaccgct, tcaacagcac, tcaaccccat, tcaacctggc, tcatcagctt, tcatcatggg, tcatcctcac, tcatctacac, tcatctactg, tcatctcctt, tcatctgctg, tcctgctggc, tcctggtggc, tccttcatcc, tctacctggc, tctgctggct, tctgggtggc, tgaacctggc, tgaccgctac, tgcccttctt, tgctcatcat, tgctgctcat, tgctgctgct, tgctggctgt, tgctggtcat, tgctggttcc, tggaccgcta, tggccatcgc, tggccatcgt, tggctgccct, tggctgggct, tgggctactg, tggtggctgt, ttcatcatca, and ttcatcatct.

48. A kit according to claim 47, produced by a process wherein step (C) includes providing, in said kit of primers, a plurality of pairs of primers, each said pair comprising
(i) a respective one of said 5' primers, and
(ii) a complementary primer of each other 5' primer, said complementary primer being referred to as a 3' primer.

49. A kit of primers for use in characterizing a sample comprising one or more nucleotide sequences, each such sequence comprising one or more nucleotides, said kit comprising primers having targeting portions for hybridizing with specific respective nucleotide subsequences, said targeting portions comprising a selected plurality of oligonucleotides selected from the group of decanucleotides consisting of aacccatca, acatcctggt, accaactact, accatgtaca, accccatcat, accgctacct, acctggccat, actacttcct, atcatctgct, atctactcca, atctgctggc, caacagctgc, caacccatc, caacctggcc, caactacttc, caccaactac, catcatctac, catcctcaac, catcctcttc, catcctggcc, catcctggtg, catctactcc, catctccatc, catctccttc, catctgctgg, ccaactactt, ccatcatcta, cccatcatct, ccccatcatc, cctcatctac, cctctgctgg, cctgctggcc, cctggaccgc, cctggccatc, ccttcatcct, ccttctacct, ccttcttcat, ctacctggcc, ccacttcctg, ctctgctggc, ctcttctggc, ctgcccttct, ctgctgctca, ctgctggctg, ctggaccgct, ctggccatcg, ctggccctgg, ctggccgtgg, ctggccttca, ctggctgccc, ctggctgggc, ctggctgtgg, ctgggctact, cttcatcatc, cttcatcctc, cttcatcctg, cttcatcgtg, cttcctgctg, cttcctggtg, gacaggtaca, gaccgctacc, gaccgctact, gcatcatcat, gccattgctg, gcccttcttc, gcctggcctg, gccttcatca, gccttcatcc, gctatgccaa, gctgcccttc, gctgctgctc, gctgctgctg, gctggccttc, gctggctgcc, gctgggctac, gctggtcatc, ggaccgctac, ggccttcatc, ggctgcccta, ggctgcccttt, ggctgggcta, gggctactgg, ggtgctgccc, gtcaccaact, gtctacctgg, gtgctggtgt, gtggaccgct, tcaacagcac, tcaaccccat, tcaacctggc, tcatcagctt, tcatcatggg, tcatcctcac, tcatctacac, tcatctactg, tcatctcctt, tcatctgctg, tcctgctggc, tcctggtggc, tccttcatcc, tctacctggc, tctgctggct, tctgggtggc, tgaacctggc, tgaccgctac, tgcccttctt, tgctcatcat, tgctgctcat, tgctgctgct, tgctggctgc, tgctggtcat, tgctggttcc, tggaccgcta, tggccatcgc, tggccatcgt, tggctgcccr, tggctgggct, tgggctactg, tggtgctgt, ttcatcatca, and ttcatcatct.

50. A kit according to claim 49, wherein said selected plurality includes between 2 and 5 of said group of decanucleotides.

51. A kit according to claim 49, wherein said selected plurality includes between 5 and 10 of said group of decanucleotides.

52. A kit according to claim 49, wherein said selected plurality includes between 10 and 30 of said group of decanucleotides.

53. A kit according to claim 49, wherein said selected plurality includes between 30 and 50 of said group of decanucleotides.

54. A kit according to claim 49, wherein said selected plurality includes more than 50 of said group of decanucleotides.

55. A kit of primers according to claim 49 comprising primers having targeting portions for hybridizing with specific respective nucleotide subsequences, said targeting portions comprising a selected plurality of decanucleotides selected from a group of oligonucleotides comprising caaccccatc, catcctggtg, catctccatc, cctggccatc, ccttcatcct, cttcctgctg, gacaggtaca, gcctggcctg, gctatgccaa, gctgctgctg, gctggctgcc, gctgggctac, ggaccgctac, ggccttcatc, tcctg(c,g)tggc, tctgctggct, tctgggtggc, tgctcatcat, tgctg(c,g)tcat, tggtgctgt.

56. A kit of primers according to claim 55, comprising a plurality of pairs of said primers, each said pair comprising (i) a respective one of said 5' primers, and (ii) a complementary primer of each other 5' primer, said complementary primer being referred to as a 3' primer.

* * * * *

UNITED STATES PATENT AND TRADEMARK OFFICE
CERTIFICATE OF CORRECTION

PATENT NO. : 6,110,667

DATED : August 29, 2000

INVENTOR(S) : Lopez-Nieto, et al.

It is certified that error appears in the above-identified patent and that said Letters Patent is hereby corrected as shown below:

Column 19, line 22, delete "3-Link" and substitute therefor --3D-Link--;

Column 61, line 12, remove the phrase "What is claimed is:".

In the Claims:

Claim 1, line 10, after "subsequence," and before "a" insert --or--;

Claim 3, line 7, delete "prier" and substitute therefor --primer--.

Signed and Sealed this

Fifteenth Day of May, 2001

Attest:

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,110,667
DATED : August 29, 2000
INVENTOR(S) : Lopez-Nietro et al.

It is certified that error appears in the above-identified patent and that said Letters Patent is hereby corrected as shown below:

Column 19,
Line 22, delete "3-Link" and substitute therefor -- 3D-Link --;

Column 61,
Line 12, remove the phrase "What is claimed is:".
Line 22, after "subsequence," and before "a" insert -- or --;
Line 49, delete "prier" and substitute therefor -- primer --.

Signed and Sealed this

Twenty-first Day of September, 2004

JON W. DUDAS
*Director of the United States Patent and Trademark Office*